United States Patent [19]
Lavin et al.

[11] Patent Number: 5,500,807
[45] Date of Patent: Mar. 19, 1996

[54] SELECTION METHOD FOR PHARMACOLOGICALLY ACTIVE COMPOUNDS

[75] Inventors: Thomas N. Lavin, Sausalito; Mark F. Norman, Petaluma; Teri E. Klein; George Seibel, both of San Francisco, all of Calif.

[73] Assignee: The Regents of the University of California, Oakland, Calif.

[21] Appl. No.: 839,170

[22] Filed: Feb. 21, 1992

Related U.S. Application Data

[63] Continuation of Ser. No. 462,608, Jan. 9, 1990, abandoned, which is a continuation of Ser. No. 294,372, Jan. 6, 1989, abandoned, and a continuation-in-part of Ser. No. 295,041, Jan. 6, 1989, abandoned.

[51] Int. Cl.$^6$ .................................................. G06F 17/11
[52] U.S. Cl. ........................ 364/496; 364/497; 364/499; 364/578
[58] Field of Search ................................. 364/496, 497, 364/578, 499

[56] References Cited

U.S. PATENT DOCUMENTS 4,982,338  1/1991  Fujita ........................................ 364/496

OTHER PUBLICATIONS

S. E. Jakes et al., "Pharmacophoric Pattern Matching in Files of 3D Chemical Structures: Evaluation of Search Performance", *Department of Information Studies, University of Sheffield*, vol. 5, #1, pp. 41–48 (Mar. 1987).
S. E. Jakes et al., "Pharmacophoric Pattern Matching in Files of 3D Chemical Structures: Selection of Interatomic Distance Screens", *Department of Information Studies, University of Sheffield*, vol. 4, #1, pp 12–20 (Mar. 1986).
Robert P. Sheridan et al., "3DSearch: A System for Three–Dimensional Substructure Searching", *Journal of Chemical Information and Computer Science*, vol. 29, pp. 255–260 (1989).
Mark G. Bures et al., "The Discovery of Novel Auxin Transport Inhibitors by Molecular Modeling and Three–Dimensional Pattern Analysis", *Journal of Computer–Aided Molecular Design*, vol. 5, pp. 323–334 (1991).
Research News, "Cancer Research: Novel Anticancer Agents Move Closer to Reality", *Science*, vol. 260, p. 1877 (Jun. 25, 1993).

*Primary Examiner*—Marianne M. Cintins
*Assistant Examiner*—K. Weddington
*Attorney, Agent, or Firm*—Phillips Moore Lempio & Finley

[57] ABSTRACT

The present invention provides a predictive method for selecting organic compounds having useful pharmaceutical activity in a mammal. The method uses volume areas of similar molecules. When specific substituents of the test compound file predetermined volumes, the compound is subject to a binding assay. Only when the binding assay is positive, is the experimental compound recommended for further pharmaceutical evaluation. Example compounds are derivatives of 4-substituted 2,6-diiodophenols of the structure:

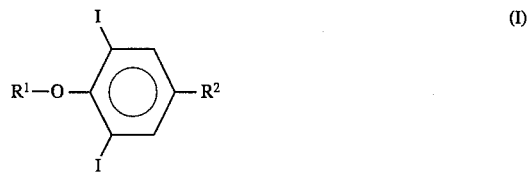

(I)

where $R^1$ and $R^2$ are defined as aliphatic or substituted aliphatic moieties or aromatic or substituted aromatic moieties. Useful structures are described. The compounds have useful pharmaceutical properties to treat conditions in a human being, including hyperthyroidism, angina pectoris, arrythmia, and the like.

10 Claims, 11 Drawing Sheets

FIGURE 1A
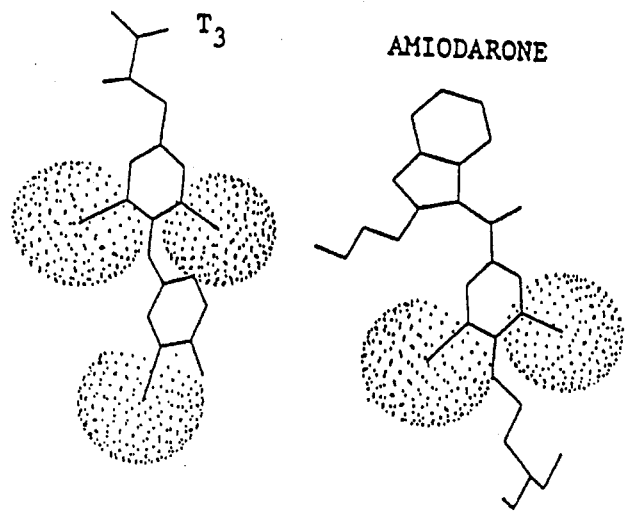
FIGURE 1B
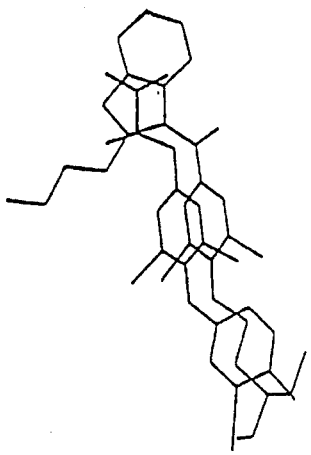
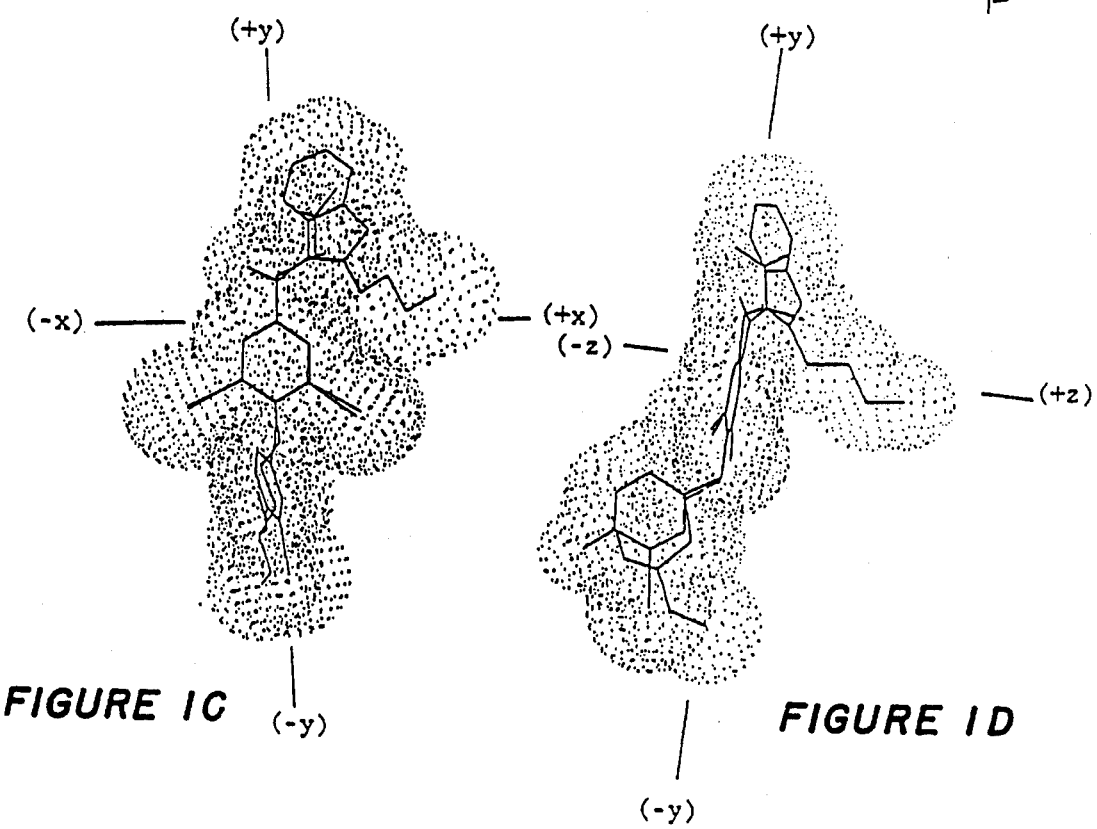
FIGURE 1C
FIGURE 1D

Triiodothyronine (MW:651)

Amiodarone (MW:645)

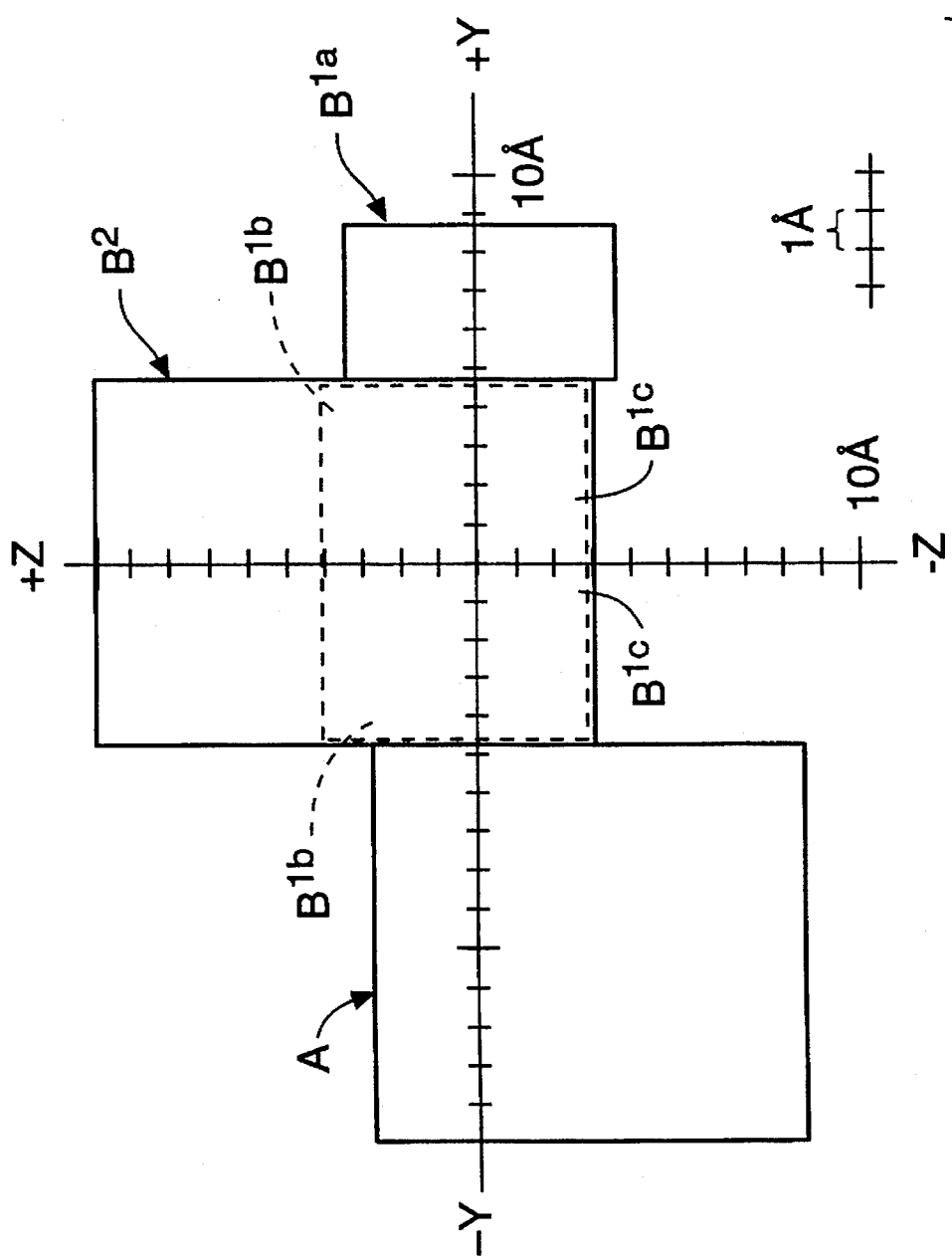
FIG._4A

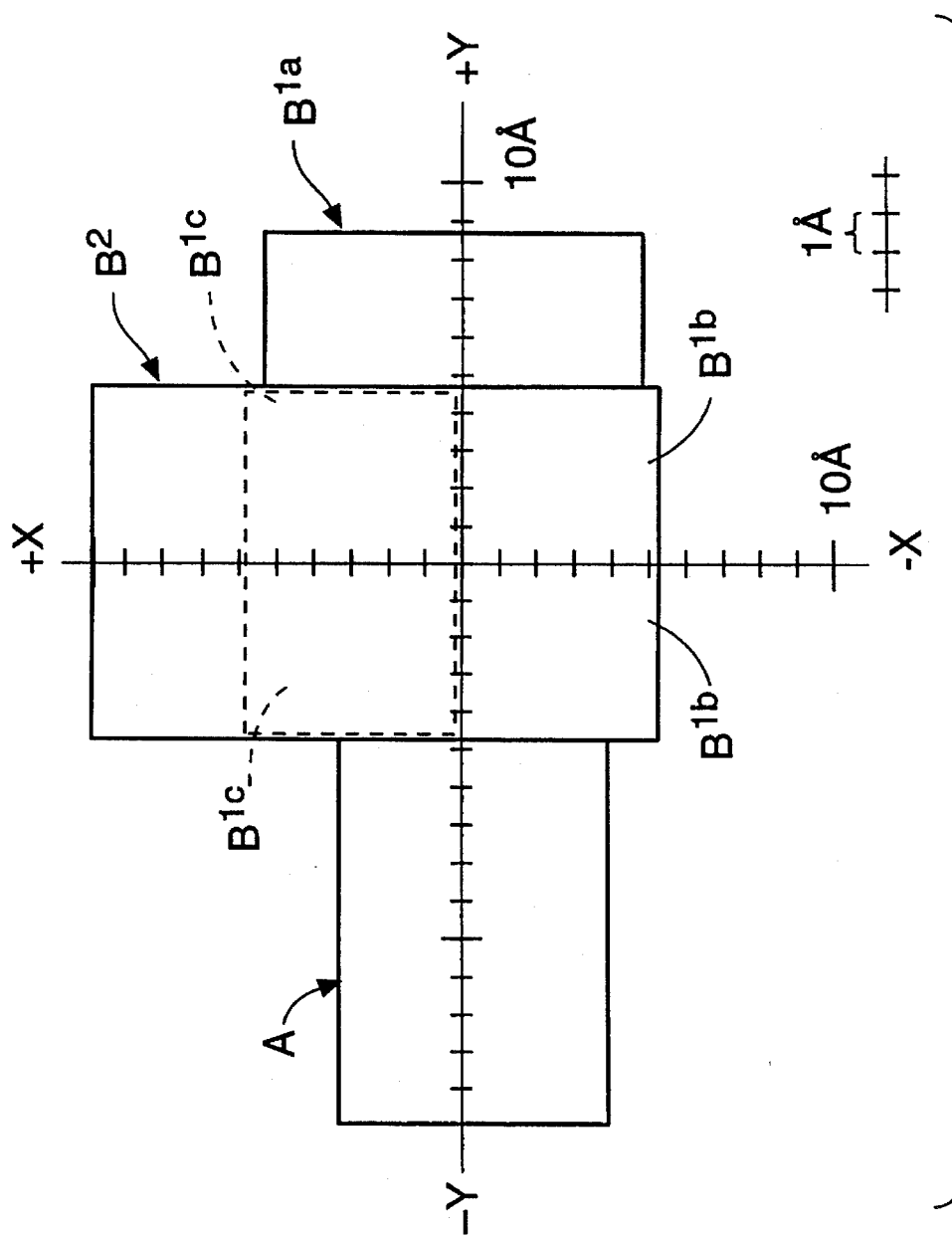
FIG._4B

Hela | 0 | .01 | .1 | 1 | 10 | NT |

Amiodarone ($\mu M$)

□ — 125I-T3
♦ — AMIODARONE

□ — 125I-T3
♦ — EXPERIMENTAL COMPOUND lab 3c

SELECTION METHOD FOR PHARMACOLOGICALLY ACTIVE COMPOUNDS

A portion of this invention was made with government support under Grants No. INRSA #AM07610-02 and #AM01329 with the U.S. National Institute of Health. The U.S. Government has certain rights in this invention.

ORIGIN OF THE INVENTION

This is a continuation of Ser. No. 462,608 filed on Jan. 9, 1990, now abandoned which is a continuation of U.S. Ser. No. 07/294,372, filed Jan. 6, 1989, now abandoned, and a continuation-in-part U.S. Serial Number 07/295,041, dated Jan. 6, 1989, now abandoned.

BACKGROUND OF THE INVENTION

1. Field of Invention

The present invention relates to a method for selecting organic compounds having useful pharmacological activity in a mammal. More specifically, the present invention provides a method for selection of pharmacologically active compounds which are 4-substituted and hydroxyl substituted derivatives of 2,6-diiodophenol according to specific spatial atom arrangements. These compounds which may themselves be novel, are designed to produce pharmacological activity. In alternative, the evaluation of known compounds according to a novel method of this invention may discover new pharmacological activity and utility.

2. Related Disclosures

Many pharmacologically active drugs act on the cellular receptor level by either mimicking the action of a natural signal molecule (agonist) or by blocking the action of the natural signal molecule (antagonist).

Natural signalling molecules are endogenous compounds which chemically effect receptors located either on the outside of the cell membrane or on the membrane of the interior subcellular structure. For example, under the normal physiological conditions there is a certain level of a neurotransmitter or signal molecule released and/or present in the vicinity of the receptors. When, for any reason, such level is disturbed, that is when there is either the excess, deficiency or lack of neurotransmitter or signalling molecule, pathological conditions such as depression, schizophrenia, Parkinson's disease, Huntington's chorea, Grave's disease or Cushing's disease and many other debilitating conditions may develop.

Consequently, most cell receptors have a developed pharmacology of agents that act as agonists or antagonists. For example, suitable antagonists are known which can block the actions of transmitters dopamine, adrenalin, noradrenalin and acetylcholine or dopaminergic, alpha and beta adrenergic, and cholinergic agonists. Antagonists have been described in *Pharmacological Basis of Therapeutics*, 7th Ed., MacMillan, N.Y. (1985) acting on the endocrine molecules interacting with mineralocorticoid, glucocorticoid, estrogen and progesterone receptors. It is surprising, however, that despite extensive pharmacological research and development of many new methodologies and laboratory techniques, certain receptors, and/or their action still remain elusive and no antagonists have been yet discovered to inhibit or modulate their activity. Thyroid hormone receptors are one of them and despite numerous structure activity studies conducted over the past 20 years, no antagonist for thyroid hormone receptor action has been identified.

Thus, it would be advantageous to have available method which would, based on certain chemical spatial arrangements, provide and allow the design of new chemical materials which would match, complement, partially block, completely inhibit, modify, accentuate or otherwise alter or effect the function of known receptors.

Numerous structure-activity studies of various endogenous chemicals and pharmaceutical drugs have suggested the necessity of bulky iodine or propyl substituents on the outer ring 3' position and the presence of a carboxylic acid group for effective receptor thyroid hormone binding and/or agonist function. *Hormonal Proteins and Peptides*, VI, 107–204 (1978), Academic Press, N.Y.; *Endocrine Rev.*, 1: 140–166 (1980).

Thyroid hormones thyronine (T4) and triiodothyronine (T3) affect the growth, development and metabolism of virtually all tissues of higher organisms. Since these hormones are endogenous, they act as agonists on the thyroid gland cell receptors known as iodothyronine receptors.

Recent studies summarized in *Proc. Nat. Acad. Sci.*, 70:3488 (1973) have demonstrated that T4 is converted to T 3 by deiodination in vivo which suggest that T4 functions as a prohormone, and all T4 biological activity, in fact, results from its conversion to T3 in vivo. High-affinity limited capacity thyroid hormone receptors have been identified in the nuclei of most tissues and the specific association between thyroid hormone and thyronine binding globulin and prealbumin, two proteins responsible for transport of the thyroid hormones to tissue sites, have also been described in *Biochemistry*, 21–163 (1982).

T3 and T4 induce a maximal 4-fold increase in the rates of growth and glucose utilization of $GH_1$ cells, a pituitary tumor cell line in cell culture. Binding studies of T3 and T4 to cellular fraction showed high-affinity, low capacity binding sites for the hormones in nuclear but not mitochondrial or cytosol fractions of the cell.

In view of the above studies, any compound which would act on iodothyronine receptors should meet the structural requirements, i.e., bulky iodine or propyl substituent on the outer 3-ring position and the presence of a carboxylic acid group together with the ability to bind to a nuclear fraction of thyroid hormone receptors.

It has, however, been recently reported that certain chemical compounds which possess neither of the required moieties nor the obvious structural similarities with T3, or T4 when their two-dimensional chemical structures are compared with these compounds, do show hyper- and hypothyroid-like activity. The drug which has been shown to have such activity but is not structurally similar to T3 or T4 is amiodarone.

Amiodarone is a benzofuran having a chemical formula (2-butyl-3-[3,5-diiodo-4-(β-diethylaminoethoxy)-benzoyl] benzofuran). Amiodarone is widely used for the treatment of angina pectoris, ventricular and supraventricular arrhythmias, which has a number of effects on parameters of thyroid function. For example, chronic administration of amiodarone has been associated with both hyper- and hypothyroid-like side effects. *Clin. Endocr.*, 22:257 (1985). The drug has also been reported to cause changes in the concentrations of serum thyroxine (T4) and triiodothyronine (T3) levels, which have been attributed to an inhibition of peripheral T4 monodeiodination, and to iodine-induced changes in glandular hormonogenesis. *J. Clin. Invest.*, 58:255 (1976). However, cases of clinical hypothyroidism have occurred, often with mildly elevated thyroid-stimulating hormone (TSH) and normal or slightly decreased T4 and T3 serum levels, which produce decreased pituitary thyroid receptor hormone binding. *Clin. Endocr.*, 22:257 (1985).

Despite the chemical and structural dissimilarities, these observations suggest that amiodarone could act as a thyroid hormone antagonist at the receptor level. If that is true, then other structurally dissimilar compounds and drugs could also possess such ability but because of their obvious chemical dissimilarity, such pharmacological ability would seldom or never be discovered.

Thus it would be very advantageous to have available method which would quickly and effectively determine whether the compound does/does not possess a pharmacological activity and whether it would act as either the agonist or the antagonist on the receptor level.

Despite the research in this area, a predictive method to select novel pharmacologically active compounds, e.g. 4-substituted and hydroxyl substituted derivatives of 2,6-diiodophenol, having useful pharmacological action in a mammal, or discovering new utilities for known compounds has not been presented. In addition, the compounds potentially predicted as having useful pharmaceutical activity may not have been disclosed or prepared.

The present invention provides such a predictive method and the compounds having a useful pharmaceutical activity in a mammal.

All references and documents cited herein are incorporated in their entirety by reference.

SUMMARY OF THE INVENTION

In the first aspect, the present invention relates to method of predicting and determining pharmacological activity of compounds having certain spatial atom arrangements.

In the other aspect, the present invention relates to a method for selecting compounds having useful pharmacological properties in a mammal from the group of compounds of structure:

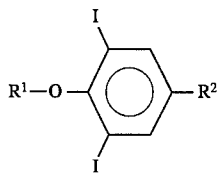
(1)

wherein $R^1$ and $R^2$ are each independently selected from aliphatic moieties, substituted aliphatic moieties, aromatic moieties or substituted aromatic moieties with the proviso that $R^1$ and $R^2$ are not both unsubstituted methyl or ethyl or a combination thereof, and when $R^1$ is —$CH_2CH_2N(CH_2CH_3)_2$, or —$CH_2CH_2NHCH_2CH_3$, $R^2$ is not,

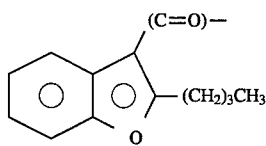

or when $R^1$ is

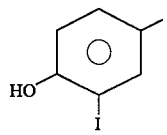

$R^2$ is not $HOC(=O)CH(NH_2)CH_2$—, which method comprises orienting the compound of structure (1) into a conventional cartesian three dimensional x, y, z coordinate space axes of FIG. 3 in a manner such that the plane of the phenyl/iodine atoms is in the x, y plane, the minus y-axis bisects the phenyl ring, and the carbon atom in the phenyl ring in the para-position to the attached oxygen atom of T-3 is fixed on the 0,0,0-coordinate having standard distances between atoms based on the carbon-carbon single bond of 1.54 angstroms, and assess the volume spatial characteristics according to the following 3-dimensional space shown in FIGS. 4A and 4B;

wherein $R^1$ is spatially within space A which is defined as between +3.5 and −3.5 angstroms on the x-axis, between −5.1 and −16 angstroms on the y-axis, and between +3 and −8 angstroms on the z-axis; and $R^2$ has van der Waals spatial characteristics comprising spaces $B^1$ and $B^2$;

wherein $B^{1a}$ is the space within −4.3 to +5.2 angstroms on the x-axis, +4.5 to +8.5 angstroms on the y-axis, and −3.5 to +3.5 angstroms on the z-axis; and $B^{1b}$ is the space within 0 and −5.0 angstroms on the x-axis, −5.1 and +4.5 angstroms on the y-axis and 4 and −3 angstroms on the z-axis, and $B^{1c}$ is defined as the space within 0 and 6 angstroms on the x-axis, −5.1 and 4.5 angstroms on the y-axis and 0 and −3 angstroms on the z-axis, and wherein $B^2$ is between 0 and +10 angstroms on the x-axis, between −5.1 and +4.5 angstroms on the y-axis and between 0 and +10 angstroms on the z-axis.

Another aspect of this invention utilizes the commercially available computer programs in preparing three dimensional spatial models of investigated molecules, which allow the superimposing of these models over the model of the standard molecule and the rotational orientation of the 3-dimensional structure for selection of pharmacologically active compounds.

In another aspect, the present invention relates to compounds of structure (1)

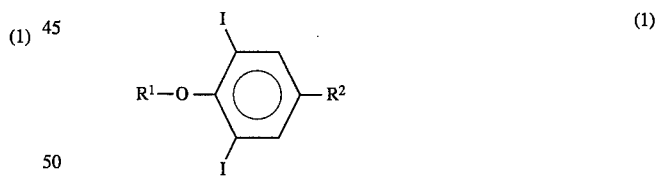
(1)

wherein:
$R^1$ is selected from:
(a) —$CH_2CH_2N(R^4)R^5$ wherein:
$R^4$ and $R^5$ are the same and are selected from —$CH_2CH_3$, —$CH_2CH_2CH_3$, —$CH_2CH_2CH_2CH_3$, —$CH_2CH(CH_3)CH_3$, —$CH_2CH_2OH$, or —$CH_2CH_2CH_2OH$; or
$R^4$ is methyl and $R^5$ is selected from —$(CH_2)_4OH$, —$(CH_2)_5OH$, —$(CH_2)_6CH_3$, —$CH_2CH(CH_3)_2$, —$CH_2$-phenyl; or
$R^4$ and $R^5$ together form —$(CH_2)_5$—, or —$CH_2CH_2O$—$CH_2CH_2$—; or
(b) —$CH_2CH_2CH_2$—$N(R^6)R$ wherein:
$R^6$ and $R^7$ are the same and are selected from —$CH_3$, —$CH_2CH_3$, or —$(CH_2)_2OH$; or
$R^6$ is methyl and $R^7$ is selected from —$CH_2CH_3$, —$CH_2CH_2CH_3$, —$CH_2$-phenyl, —$CH_2CH_2OH$, or —$CH_2CH_2CH_2OH$; or

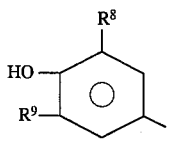

wherein:
R$^8$ and R$^9$ are both —CH(CH$_3$)$_2$, or R$^8$ is —H, and R$^9$ is —(CH$_2$)$_5$OH, or R$^8$ is —H and R$^9$ is —I; and
wherein:
R$^2$ is selected from

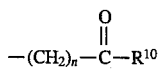            (a')

wherein n is 0, 1 or 2; and
wherein when n is 0, R$^{10}$ is —OH, or —CH$_3$,

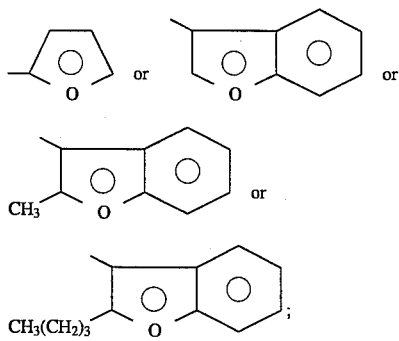

and
  wherein when n is 1, R$^{10}$ is —OH, or

and
  wherein when n is 2, R$^{10}$ is

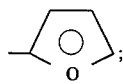

or

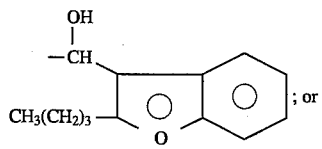            (b')

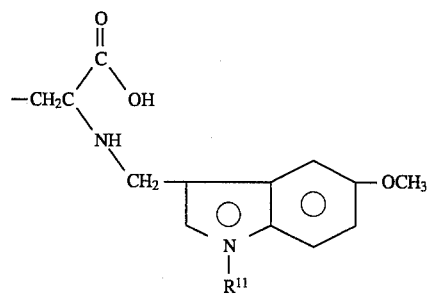            (c')

wherein R$^{11}$ is selected from —H, —(C=O)-phenyl, or para(CH$_3$O)-phenyl-;
with the proviso that when R$^1$ is

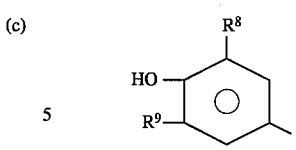            (c)

and R$^2$ is (a') when n is 0 or 1, then R$^{10}$ is not OH.

BRIEF DESCRIPTION OF DRAWINGS

FIG. 1 shows computer-generated models of T3 and amiodarone in a nondeformed state.

FIG. (1A) shows van der Waals forces associated with the iodine atoms illustrated for each molecule. Triodothyromine T3 is on the left, amiodarone on the right.

FIG. 1(B) shows hypothetical alignment of molecules along their respective "vertical" axes.

FIG. 1(C) shows superimposition of diiodo phenyl rings showing similarity of space filling by surface van der Waals forces.

FIG. 1(D), shows superimposition of diiodo phenyl rings showing similarity of space filling by surface van der Waals forces, with 90° C. rotation along vertical axes. Slight changes in amiodarone torsional angles increases the similarity of the superimposition of amiodarone and the "lower" outer ring of triiodothyronine.

Figure 2B:
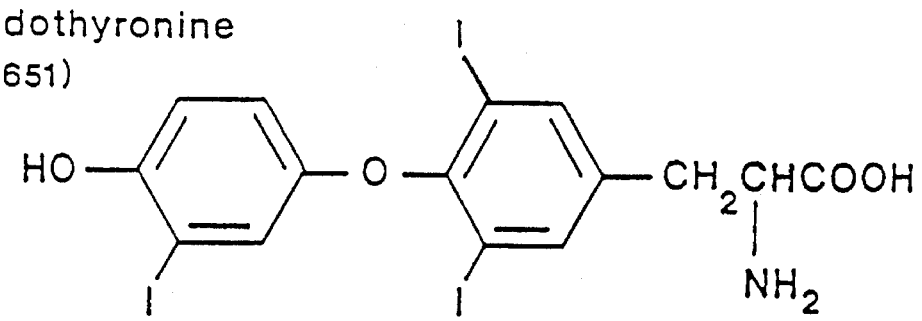
Figure 2A:
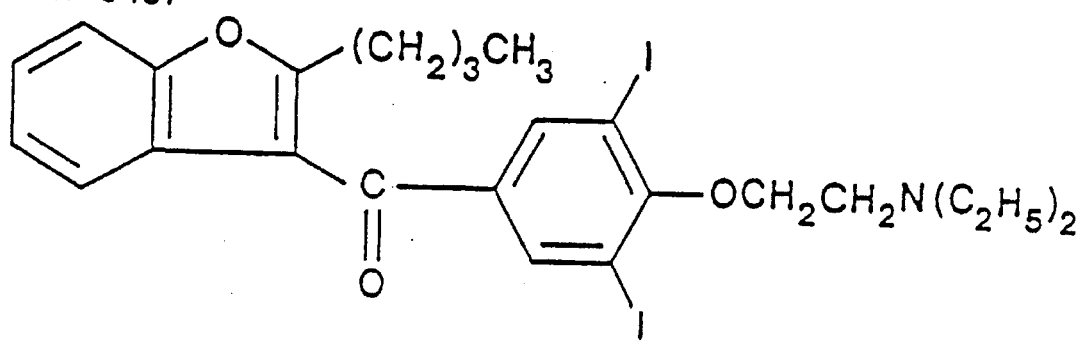

FIG. 2 shows two chemical structures. FIG. 2A shows amiodarone structure. FIG. 2B shows trioodothyronine structure, also designated T3.

Figure 3:
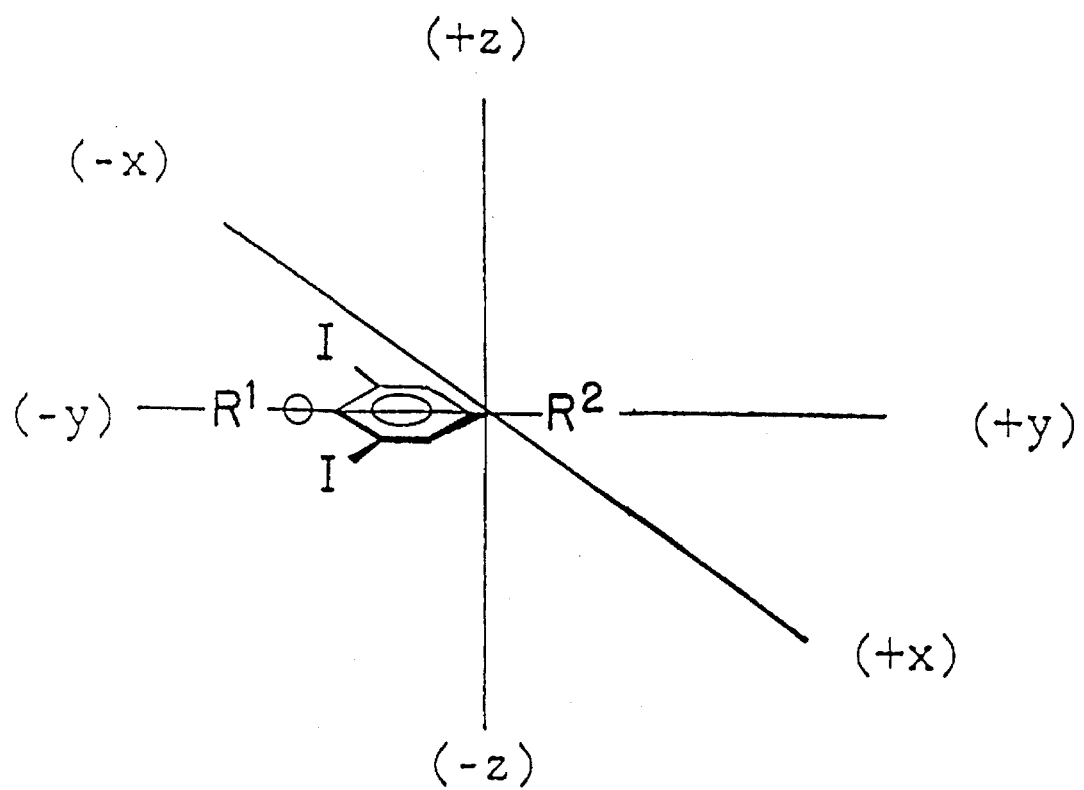

FIG. 3 depicts a conventional cartesian three dimensional x, y, z coordinate space axes and the orientation of the diiodophenyl ring of structure (1).

FIGS. 4A and 4B are spatial models of three dimensional x, y, z coordinate space axes depicting space A and space B as projected on the y-z and x-y planes where R$^1$ substituent of the structure (1) is spatially within space A and R$^2$ substituent of the compound (1) is within space B.

Figure 5:
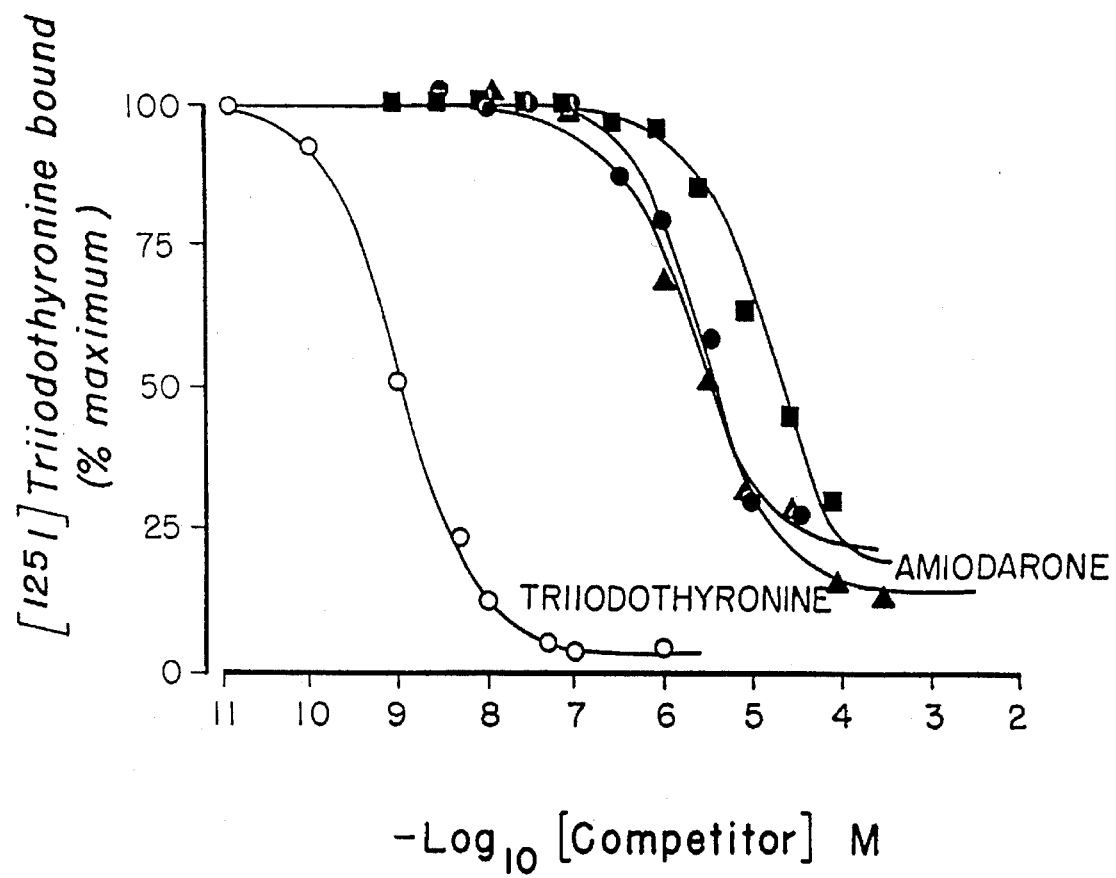

FIG. 5 illustrates competition by amiodarone and T3 for binding of L$^{125}$I-T3 to nuclear thyroid hormone receptors from different tissues.

FIGS. 6 as 6A and 6B illustrates the competitive nature of the effects of amiodarone on saturation binding of T3 to soluble nuclear thyroid hormone receptors.

Figures 7, 7A, 7B:
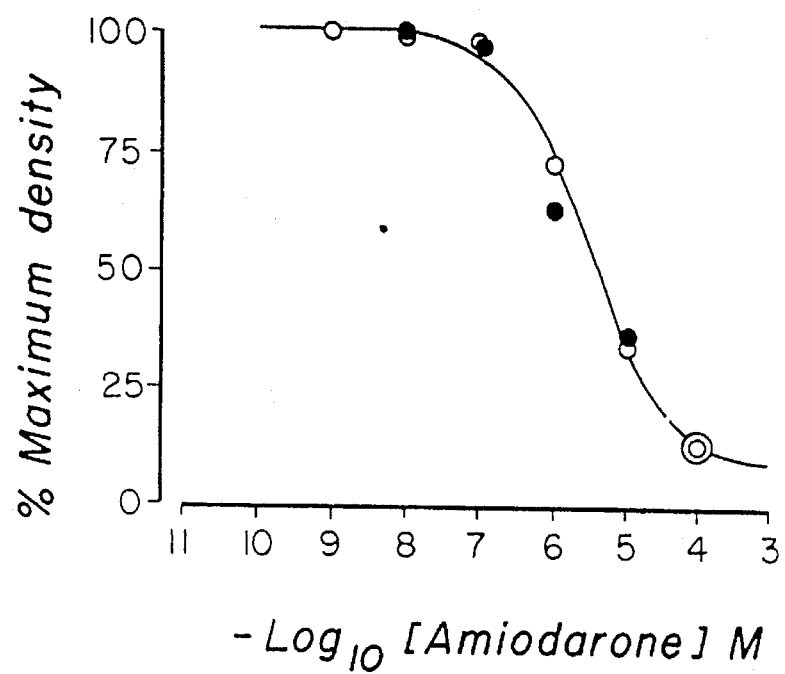

FIG. 7A is an autoradiograph which shows the effects of increasing concentration of amiodarone on accumulation of rGH mRNA in the presence of T3.

FIG. 7B is a graphic representation of FIG. 7A showing the effects of aminodarone on accumulation of rGH mRNA in cultured GC cells by plotting % Maximum density versus -Log$_{10}$ (amiodarone) M.

Figure 8:
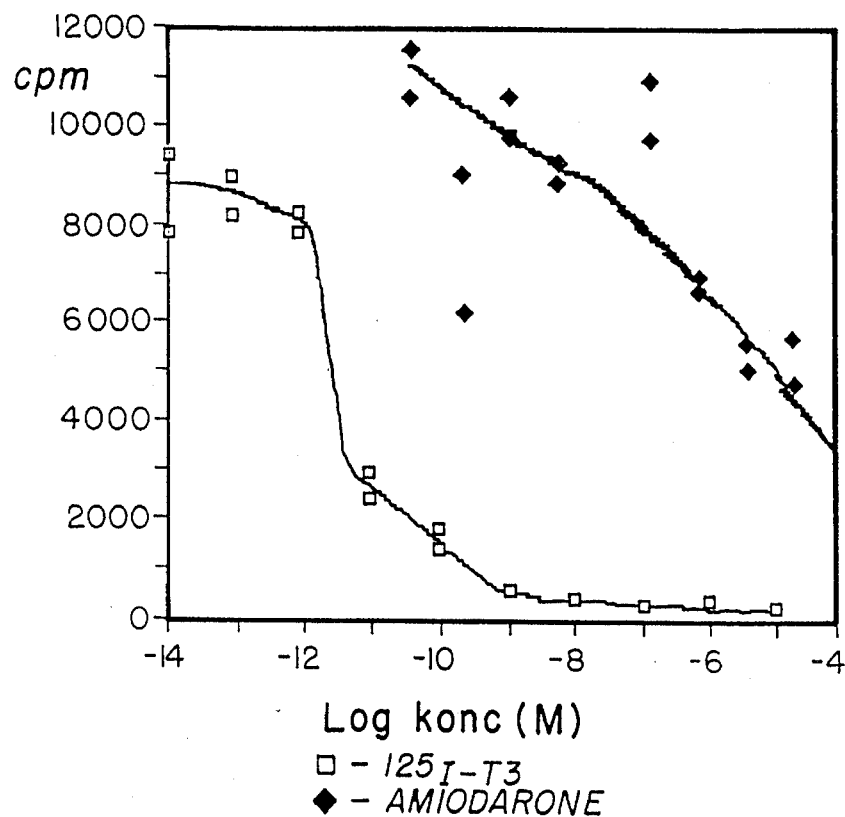

FIG. 8 depicts receptor binding of T3 and amiodarone.

Figure 9:
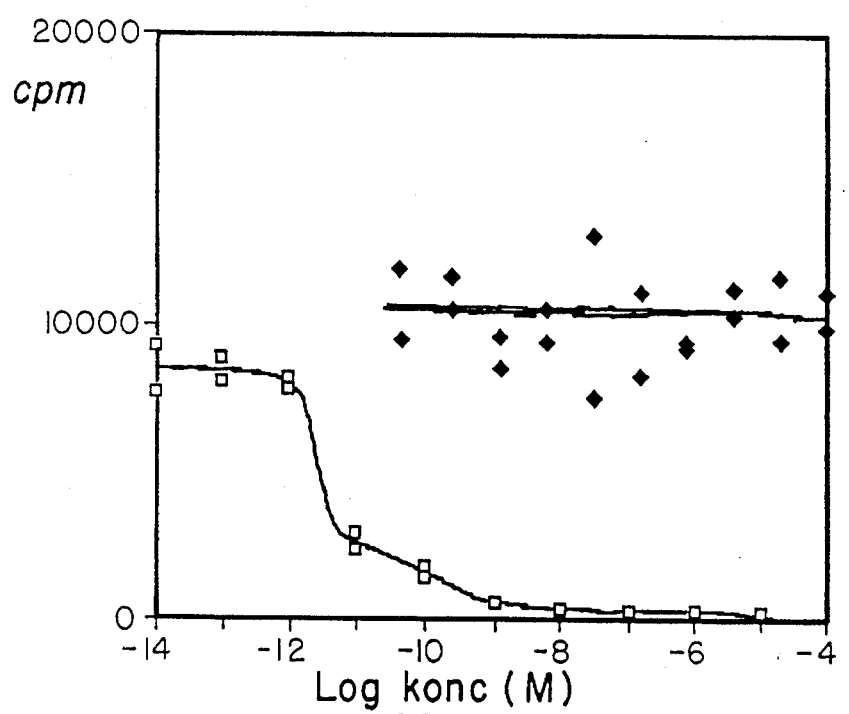

FIG. 9 depicts receptor binding of T3 and of the experimental compound (1) wherein R$^1$ is as shown in Table 1 where R$^4$ and R$^5$ are both 1a, and R$^2$ is 3c, as shown in Table 2.

Figure 10:
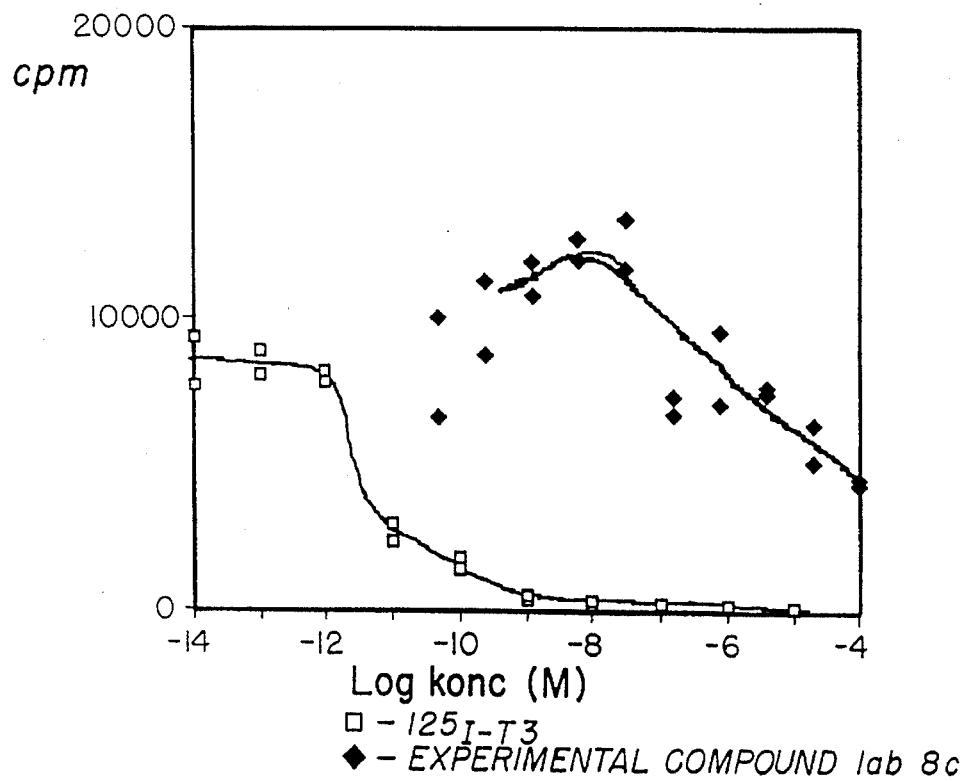

FIG. 10 depicts a receptor binding of T3 and of the experimental compound (1) wherein R$^1$ is as shown in Table 1 where R$^4$ and R$^5$ are both 1a, and R$^2$ is 8c, as shown in Table 2.

Figure 11:
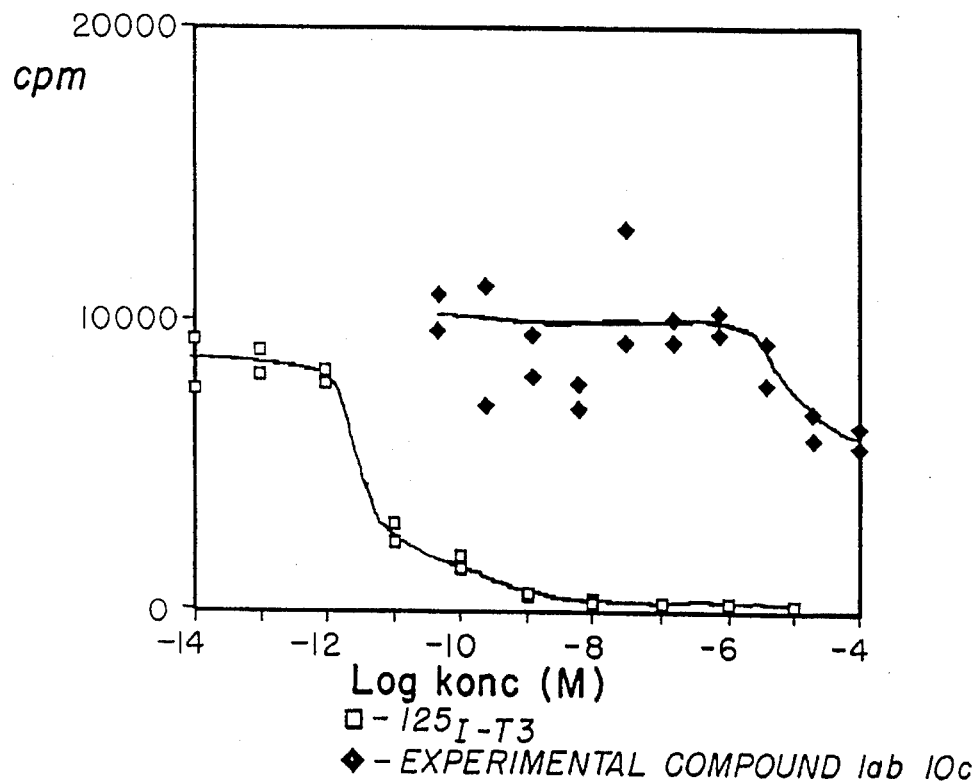

FIG. 11 depicts receptor binding of T3 and of the experimental compound (1) wherein R$^1$ is as shown in Table 1 wherein R$^4$ and R$^5$ are both 1a, and R$^2$ is 10c, as shown in Table 2.

Figure 12:
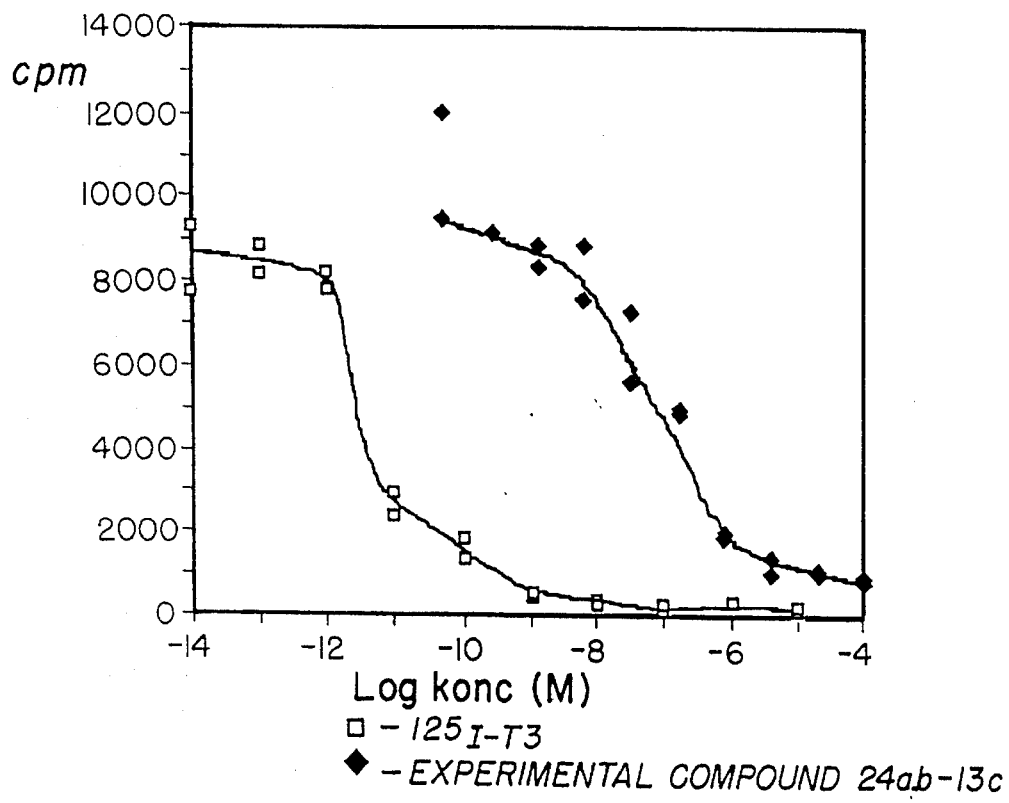

FIG. 12 depicts receptor binding of T3 and of the experimental compound (1) wherein $R^1$ is 24a, as shown in Table 1, and $R^2$ is 13c, as shown in Table 2.

Figure 13:
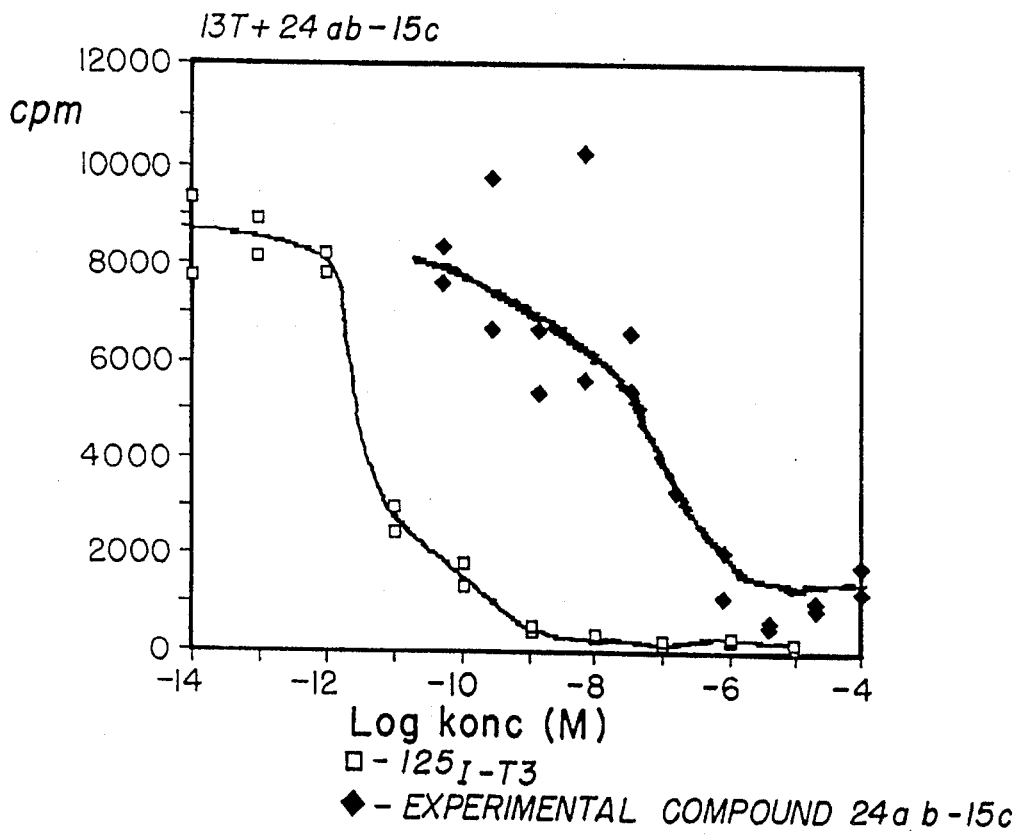

FIG. 13 depicts a receptor binding of T3 and of the experimental compound (1) wherein $R^1$ is 24a, as shown in Table 1 and $R^2$ is 15c, as shown in Table 2.

DETAILED DESCRIPTION OF THE INVENTION

This invention concerns a novel method of predicting, evaluating, and designing pharmacological activity of the experimental compounds on the basis of their spatial atom arrangements. Three dimensional spatial model has been developed based on conventional cartesian three dimensional x, y, z coordinate space axes within which the structure of standard compound, having the predetermined desirable pharmacological activity, is entered by using conformation van der Waals characteristics. The three dimensional structure model of the experimental compound of which the pharmacological activity is evaluated, with respect to the mimicking of the pharmacological activity of the standard compound, is superimposed on the three dimensional spatial model of the standard compound in a manner similar to that of the standard compound, and the structure of the experimental compound is oriented by rotation on x, y, z plane to become spatially as close as possible to that of the standard compound. This is achieved by superimposing the same segment of the experimental and standard molecule and by rotating each substituent of the experimental molecule in such a manner that it fits within the certain space which has defined x, y, z coordinates on both plus (+) and minus (−) sides of the x, y, z axes plane, as shown in FIG. 3 and FIGS. 4A and 4B, within which each substituent of the standard compound is located and positioned.

The first precondition for the experimental compound to have the same or similar pharmacological activity of the standard compound (e.g., Structure 1) is that the substituents of the experimental compound must fit within the predefined volumes and spaces within which the substituents of the standard compound fit. If the two or more remotely located substituents, for example $R^1$ and $R^2$, of the experimental compound fit in the same spaces as substituents of the standard compound, that is in space A, space $B^{1b}$, $B^{1c}$ and $B^{1a}$, and a small portion of less than 10%–20% fits in space $B^2$, there is a good chance that the experimental compound will have the same or similar pharmacological activity, that is, that it is an agonist acting on the same receptors as the standard compound. On the other hand, if only one substituent of the experimental compound is located within the space defined for and usually occupied by the substituent of the standard compound and additional volume of the other substituent is occupied by the volumes defined in $B^1$ and $B^2$, with the other substituent occupying greater than 10–20% of space $B^2$, then the pharmacological activity of the experimental compound is likely to be antagonistic, i.e. acting, for example, as an inhibitor of the standard compound.

By the way of the example, this invention is practiced by using as a standard compound a thyroid hormone T3, having a well defined and specific regulatory and metabolic agonist function on the thyroid cell receptors, and by using as an experimental compound the known antiarrhythmic drug amiodarone. Structurally, these two compounds, i.e. standard compound T3 and experimental compound amiodarone, differ. Except of the 2,6-diiodophenyl, which is present in both compounds, their substituents, as shown in FIG. 2, are different. When however, the diiodophenyls of both compounds are superimposed and fitted into the three-dimensional model of this invention, their similarity is easily ascertainable, as seen in FIG. 1D. Angstrom atomic coordinates of both compounds using the defined 0,0,0 point are shown in Tables 1A and 1B.

TABLE 1A

| T3 Å Coordinates for Atoms ± .25 Å | | | |
|---|---|---|---|
| | X | Y | Z |
| C1 | 0 | 0 | 0 |
| C2 | −1.17 | −.8 | 0 |
| C3 | −1.17 | −2.1 | −.1 |
| C4 | 0 | −2.8 | −.2 |
| C5 | 1.24 | −2.1 | −.2 |
| C6 | 1.24 | −.8 | −.1 |
| I-5 | 3.1 | −3 | −.4 |
| O-4[(1)] | 0 | −4.2 | −.27 |
| C1' | 0 | −4.9 | −1.5 |
| C2' | .42 | −6.2 | −1.4 |
| C3' | .4 | −6.9 | −2.6 |
| C4' | .15 | −6.3 | −3.9 |
| C5' | −.3 | −5 | −3.9 |
| C6' | −.4 | −4.3 | −2.7 |
| O-4'[(2)] | .2 | −7.1 | −5.0 |
| I3' | .8 | −9. | −2.6 |
| I3 | −3 | −3.0 | −.3 |
| C-7 | 0 | 1.5 | −0 |
| C-8 | 1.3 | 2.1 | +.5 |
| C-9 | 1.3 | 3.6 | .35 |
| O-10 Carbonyl | .8 | 4.1 | −.6 |
| O-9 | 1.9 | 4.3 | 1.2 |
| N-8 | 1.4 | 1.8 | 1.9 |

[1]Ring Bridge Oxygen
[2]OH Oxygen

TABLE 1B

| Amiodarone Å Coordinates for Atoms ± .25 Å | | | |
|---|---|---|---|
| | X | Y | Z |
| C1 | 1.5 | 6.1 | .6 |
| C6 | 2.3 | 5.3 | 1.2 |
| C5 | 2.0 | 4.0 | 1.1 |
| O-7 Furan | 2.8 | 3 | 1.66 |
| C8 | 2.0 | 1.9 | 1.4 |
| C10 | 2.4 | .6 | 2.1 |
| C11 | 3.0 | .8 | 3.5 |
| C12 | 3.4 | −.5 | 4.2 |
| C13 | 3.9 | −.3 | 5.6 |
| C9 | .9 | 2.2 | .6 |
| C4 | .9 | 3.5 | .5 |
| C3 | .1 | 4.4 | 0 |
| C2 | .4 | 5.7 | 0 |
| C14 | −0.1 | 1.4 | .2 |
| O-15 Carb | −1.1 | 1.9 | 0 |
| C-16 | 0 | 0 | 0 |
| C-21 | −1.1 | −7 | 0 |
| C-20 | −1.1 | −2.1 | −.14 |
| C19 | 0 | −2.8 | −.25 |
| C-18 | +1.1 | −2.0 | −.25 |
| C-17 | +1.1 | −.7 | −.1 |
| I11 | 2.9 | −3.0 | −.5 |
| O-22 Ring | .2 | −4.1 | −.35 |
| C-25 | −.3 | −5 | −1.4 |
| C-26 | .2 | −6.4 | −1.1 |
| N-27 | −.2 | −7.4 | −2.1 |
| C-30 | +.3 | −7.1 | −3.5 |
| C-31 | 0 | −5.7 | −4.0 |
| C-28 | +.2 | −8.8 | −1.6 |
| C-29 | −.3 | −9.2 | −.34 |
| I-10 | −3.0 | −3.2 | −.22 |

Once such structural similarity is proven, the pharmacological activity, whether agonist or antagonist, is almost certainly present. Such activity is then quickly determined by the receptor binding assay. Only when both the structural spatial similarity exist and the binding to the receptor is positive, the compound is suitable for broad pharmacological testing with reasonable probability that either agonist or antagonist activity of the drug exist, making it worthwhile for extensive pharmacological testing and development into a pharmacological drug.

Since the broad range of pharmacological tests are generally necessary to determine whether or not there is or there is not a pharmacological activity present, the current invention represent a substantial savings of the resources and money. In view of the thousands of newly synthesized compounds of which pharmacological activity must be determined, the magnitude of savings achieved by this invention is easily apparent. By simply using two tests, one computerized, the second simple receptor binding assay in the laboratory, the need for further pharmacological testing is easily confirmed or disproved.

Moreover, due to a seeming one or two dimensional structural dissimilarity, many compounds would never even be tested for certain pharmacological activity since such activity would not be expected from their one or two dimensional chemical structures.

Consequently, the current invention also provides for discovery of new pharmacological activities for compounds where it would not be expected or suspected, and therefore would not be tested for.

Finally, the current invention is useful in predicting and designing new compounds based on pharmacological activity of known compounds. By way of example, when compound X is known to have certain desirable pharmacological activity, but its substituents confers on it rather undesirable side effects, the practice nowadays is that the closest possible structures are designed and the substituents responsible for the side effects are changed. Each new derivative is tested, until the undesirable properties are either eliminated or decreased to the acceptable level. By utilizing the current invention, the compound which is not necessarily structurally similar but which fits the spatial model of this invention may be designed by combining the molecular components responsible only for desirable pharmacological properties, regardless whether these components combined together are structurally similar or not.

The current invention thus provides fast, easy, and reliable method for evaluation of pharmacological activity of large number of compounds. This method eliminates unnecessary laboratory testing which is costly, laborious and slow and which is currently based primarily on the structural similarity to standard compound of which pharmacological activity is the new compound supposed to mimic, substitute or countermand.

PREFERRED EMBODIMENTS

Preferred embodiments of this invention are compounds which fits within three dimensional spatial model of the standard compound having certain predetermined pharmacological activity.

More preferred embodiments of this invention are compounds chosen by the method of this invention from the group of compounds of structure

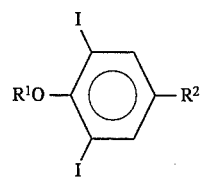

(1)

wherein $R^1$ and $R^2$ are each independently selected from aliphatic, substituted aliphatic, aromatic or substituted aromatic moieties with the proviso that $R^1$ and $R^2$ are not both at the same time unsubstituted methyl or ethyl or combination of both and when $R^1$ is —CH$_2$CH$_2$N(CH$_2$CH$_3$)$_2$ or —CH$_2$CH$_2$NHCH$_2$CH$_3$, $R^2$ is not

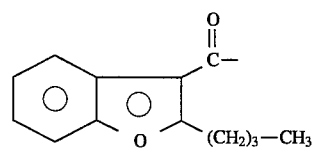

or when $R^1$ is

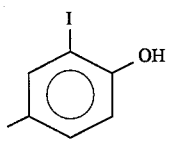

$R^2$ is not HOC(=O)CH(NH$_2$)CH$_2$—.

Still another aspect of this invention are compounds where embodiment $R^2$ has at least four atoms, preferably selected from carbon, oxygen, nitrogen optionally sulfur or combinations thereof.

More preferred embodiments are the compounds chosen by the method of this invention wherein the three dimensional model of the standard and experimental compounds are superimposed over each other and the spatial similarity is found suggesting pharmacological activity which is confirmed by receptor binding assay.

Another aspect of this invention are the compounds having substituents in the predetermined spaces and volumes, in which a binding evaluation is undertaken. Only when the binding assay is positive, the experimental compound is recommended for further pharmacological evaluation.

DEFINITIONS

"Aliphatic moiety" refers to alkyl, alkenyl, acetylenyl, cyclic, acyclic and the like compound having between about 1 to 20 carbon atoms. Acids, ketones, aldehydes, alcohols, sulfides, amines, imines, and the like and combinations thereof are found within the aliphatic groups. Preferably the aliphatic moiety has about 1 to 10 carbon atoms.

"Aromatic moiety" refers to a cyclic compound which has from about 5 to 25 carbon atoms, having conventional aromatic properties. Compounds include benzene, toluene, naphthalene, hexane, heptane and the like. Heterocyclic compounds (groups) may have one or more carbon atoms in a ring replaced by at least one polar atom such as oxygen, nitrogen, sulfur and the like. Combinations of hetero atoms are contemplated.

"Substituted aromatic moiety" refers to aromatic groups as defined herein wherein at least one ring proton is substituted by a group such as hydroxy, chloro, bromo, iodo, amino, —SH, —COOH, —C=O, CH(=O), and the like.

"Pharmaceutically acceptable acid addition salt and ester" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ehtanesulfonic acid, p-toluenesulfonic acid, salicylic acid and the like. The pharmaceutically acceptable acid addition salts and esters are intended to be included in the present invention of Structure (1).

"Substituted aliphatic moiety" refers to aliphatic moiety which has one or more protons substituted by a polar atom or combinations thereof selected from oxygen, nitrogen, sulfur.

"STANDARD compound" means any pharmacologically active compound of which three dimensional spatial atom arrangement can be made into three dimensional computerized model using the van der Waals characteristics.

"Experimental compound" means any compound of which three dimensional spatial atom arrangement can be made into three dimensional computerized model using the van der Waals characteristics.

Amiodarone biologically fulfills the criteria of a thyroid hormone antagonist. The drug behaves as a competitive inhibitor of triiodothyronine (T3), binds to solubilized thyroid hormone receptors, and blocks both receptor binding and the biological effect of thyroid hormone when administered to hormone-responsive cells in culture. *J. Clin. Invest.*, 83: (1989).

Structure-activity studies have suggested the necessity of bulky iodine or propyl substituents on the outer ring 3' position and the presence of a carboxylic acid group for effective receptor binding. Amiodarone possesses neither of these moieties, and indeed comparison of the two-dimensional chemical structures reveals no obvious structural similarity between the drugs.

The biological activity which points toward antagonistic activity of amiodarone to thyroid hormone is in direct disagreement with its structure. As seen in FIG. 2A depicting amiodarone and in FIG. 2B depicting T3, while their molecular weight of M.W. 645 and M.W. 651, respectively, is fairly close, their chemical structural formula is very dissimilar. In fact, the only identical structural component present in both compounds is the aromatic moiety 2,5-disubstituted with iodine. Consequently, seemingly there is no structural similarity in one dimensional chemical structure.

Similarly, comparison of both structures two-dimensionally reveals no obvious structural similarity between both structures, since the amiodarone possesses no carboxylic iodine or propyl group substituents on the 3-position of the outer aromatic drug which is believed to be necessary for effective receptor binding and agonist function (*End. Review*, 1:140 (1980).

And yet, both compounds seem to clearly interact with the same receptor. Thus, if there is some possible structural similarity between T3 and amiodarone, it must be in some spatial arrangement of atoms which assures the binding of amiodarone to the receptors identical to those which bind to thyroid hormone.

The FIG. 1A shows van der Waals forces which are associated with iodine atoms substituting the aromatic ring 2,5-positions in both T3 and amiodarone molecules. When the both molecules were aligned, hypothetically, along their respective vertical axes, as shown in FIG. 1B, the only points of similarity are the aromatic rings with two iodines sticking out, and a partially similar aliphatic chain parallel to each other in position 1 and 4. There the similarity ends.

When, however, as shown in FIG. 1C, both molecules were superimposed over their diiodo phenyl rings, they showed similarity of space filing by surface van der Waals forces and when, as in FIG. 1D, these structures were rotated 90° along their respective x, y and z axes, the similarity was readily visible, particularly the similarity of the $R^1$ substituent of amiodarone and the lower outer ring of T3. This similarity may be increased by slight changes in amiodarone torsional angles.

If such biological-spatial relationship exists between T3 and amiodarone, they presumably exist also for other seemingly structurally unrelated molecules seemingly and it is therefore a primary object of this invention a) to provide a method for testing currently known molecules having non-similar structures to the endogenous or synthetic known agonists or antagonists, b) to design new molecules having the similar superimposable structural similarities and characteristics and c) to provide a fast and efficient method for testing of the new and known molecules by using the system of this invention combined with the biological evaluation of the molecules, namely combined with binding receptor assay used to determine quickly whether spatial arrangements of the molecules has the expected biological activity.

Determination of Spatial Atom Arrangements

The spatial atom arrangements of the molecules which are candidates to be used in practice of this invention, are determined by choosing a standard molecule which is either endogenous hormone or neurotransmitter, or synthetic pharmaceutical drug which acts as an agonists or antagonist in certain biological set-up, and is pharmacologically active on certain receptors. Then, a extended conformation molecular model, using standard data sets, of the standard molecule is constructed. The molecular model is constructed with the MIDAS program developed and available from the Computer Graphics Laboratory, University of California, San Francisco, Calif. The model is based on using a standard data set and refined using a program such as MM2®.

Using the MIDAS® computer software program, publically available from the University of California, San Francisco program, computer generated van der Waals surfaces are displayed around the various atoms forming the standard molecule. The model of the standard molecule is then oriented into a conventional cartesian three dimensional x, y, z coordinated space axes, described in *Advanced Physical Chemistry*, McMillan Co., UK (1969), in a certain manner which is specific to each molecule but which orients on the x, y, z axes. The portion of the molecule which is important functionally and substituents which may or may not be functionally important, as determined from the standard compound, are then superimposed over the same components of the standard molecule. The molecular substituents are then individually determined to be within certain or volume space which has been herein designated to be space A for substituents $R^1$ which is defined, in angstroms, as a distance in plus and minus angstroms on the x, y or z axes, or as a space between plus and minus places, expressed in angstrom, on the x, y, or z axes shown in FIG. 3. Similarly, substituent $R^2$ is determined to be spatially within certain spaces and volumes, herein called space B, again expressed in distances in plus and minus in angstrom on x, y, and z-axis. In similar manner, all substituents of the standard molecule are placed in certain determined space defined on axes x, y and z in minus and plus space or volume of each axis. The spaces A and B are illustrated in FIGS. 4A and 4B. In this particular case, the space A determines and limits spatial atom arrangement of substituent $R^1$, and space B determines atom arrangement of the substituent $R^2$.

When the spatial model for standard active molecule is prepared, using the same procedure, the model of the second experimental molecule is then prepared in the same way.

If the experimental molecule is a known chemical which has seemingly different chemical structure but similar biological activity, both models are superimposed over each other and the structural spatial similarity is determined. If such spatial similarity exists, combined with its biological activity, then the proof is obtained that the experimental molecule is binding to the same receptor which also binds the standard molecule.

If the chemical structure of the experimental molecule is not known and the new molecule is to be designed having similar biological and pharmacological activity, than the model of the standard molecule is used to design a number of structurally similar compounds, in spatial arrangement, similar to the standard compound. The model of the designed compound is then superimposed over the model of the standard compound and those compounds which are spatially similar to standard compound are tested for their biological activity.

Thus, using the procedure of this invention, a large number of compounds may be quickly and easily examined and the expensive and lengthy testing avoided. Moreover, the need for actual synthesis of many compounds is effectively eliminated because only those compounds which are spatially similar to the standard compound, will be synthesized and tested pharmacologically.

The commercial computers used in this invention are VAX® computer, (a trademark of the Digital Equipment, Company (DEC) of Maynard, Mass., using publicly available VMS® computer hardware, a trademark of the Digital Equipment Co. of Maynard, Mass., and a UNIX® computer operating system, (a trademark of the AT&T Co., New York, N.Y.

The Quantum Chemistry Program Exchange (QCPE), Department of Chemistry, Indiana University, Bloomington, Ind., publicly available MM2® computer software program (a trademark of Tripos Associates, of St. Louis, Mo. is used to refine the coordinates for amiodarone and T3, or in alternative the T3 coordinates are extracted from the publicly available Cambridge Crystallographic Structural Data Base, Cambridge University, Cambridge, England.

Commercially available drug design computer programs of interest also include, for example, program SYBYL® computer software program, a trademark of Tripos Associates, St. Louis, Mo.; or BIOGRAF® computer software program, Biodesign, Inc., Pasadena, Calif.

The interatomic distances for benzene or other C=C, C—N, C—O, C=O, etc. are found in *Chemistry of Organic Compounds,* 2nd Ed., C. R. Noller, W. B. Sanders Company Philadelphia, Pa. (1957).

For computer modeling, the VAX® computer hardware system is loaded with VMS® or UNIX® operating computer software system, which is commercially available.

The coordinates for the atoms of amiodarone from a standard data set are input into the VAX® computer program and refined by using the MM2® computer software program.

The coordinates for the atoms of T3 are input into the VAX® computer hardware system. Additionally, the BIOGRAF® computer software program may be added to the VAX® computer hardware system.

By manipulating the computer program of the spatial structural atoms of amiodarone and T3, as shown in FIG. 1B, it is apparent that the diiodophenol rings in each are essentially superimposable.

From this spatial relationship, the surprising essential spatial features of pharmacologically active molecule is obtained. These spatial features then are useful to select compounds which have useful pharmacological properties and may interact with the receptors in the cells of a human being to mitigate, alter, inhibit or otherwise affect the disease conditions described herein.

According to this method, it is observed that both T3 and amiodarone occupy $R^1$ space A but that amiodarone significantly contributes to space $B^2$ much of which is not occupied by the T3 molecule. Substitutions of N-acyl groups in a portion of this area, described in *Biochemistry,* 21:163 (1982), led to diminished binding and agonist activity. Amiodarone does not contain the polar N-acyl groups but instead uses a non-polar and flexible hydrocarbon moiety.

This observation suggests that substitutions containing alkyl groups in $B^2$ space but without N-acyl moieties, to T3 or other thyroid hormones analogs such as thyroid hormone-acetic acid, might product antagonist activity.

In defining $R^1$ and $R^2$ groups for spatial characteristics, the groups are predominantly (substantially) within space A for $R^1$ and $B^1$ and $B^2$ for $R^2$. At least 90% of the structure is within these spaces. Space filling of $B^2$ with atoms of the structures described herein is preferred.

From the conformation studies, it is assumed that either T3 conformation is not markedly deformed by the receptor in the process of receptor binding or that both T3 and amiodarone or other antagonist and derivatives thereof are sufficiently flexible to allow similar degrees of deformation. Spaces $B^1$ and $B^2$ could conceivably occur in the mirror image location via rotation, e.g. 180°, around the C—C bond between the ketone and phenyl moiety located in space B between 0, 0, 0 (x, y, z) and approximately 0, 1.5, 0 angstrom. This conformation could equally occur in T3. Consequently the space B can be as shown or in its rotational image space $B^{2'}$.

In a preferred embodiment, for this particular pair of compounds, the coordinates for $R^1$ (space A) are between about 3, −3 angstroms on the x-axis, −2.5 to −12 angstroms on the y-axis, and +2.0 to −7 angstroms on the z-axis, and for $R^2$ space $B^1$ and $B^2$ where $R^2$ has van der Waals spatial characteristics comprising spaces $B^1$ and $B^2$. $B^1$ is the area falling outside $B^2$. In the case of T3 and amiodarone examples shown in FIGS. 1C and 1D, $B^2$ is defined by two sets of coordinates:

$B^{1a}$ is defined as the space within −4.3 to +5.2 angstroms on the x-axis, +4.5 to +8.5 angstroms on the y-axis, and −3.5 to +3.5 angstroms on the z-axis, and $B^{1b}$ is defined as the space within 0 and −5.0 angstroms on the x-axis, −5.1 and +4.5 angstroms on the y-axis and 4 and −3 angstroms on the z-axis, and $B^{1c}$ is defined as the space within 0 and 6 angstroms on the x-axis, −5.1 and 4.5 angstroms on the y-axis and 0 and −3 angstroms on the z-axis, and $B^2$ is between about 0 to +8 angstroms on the x-axis, +3.1 to −2.8 angstroms on the y-axis, and between 0 and +8 angstroms on the z-axis.

Since the amiodarone was already shown to have all properties needed in practicing this invention, it was used as the model of experimental compound.

To explore a possible structural similarity between T3 and amiodarone, extended conformation molecular models, as shown in FIG. 1 using standard data sets, were constructed with the MIDAS® program as described above. FIG. 1A displays triiodothyronine (left) and amiodarone (right), each with computer-generated van der Waals surfaces displayed around their respective iodine atoms. When the diiodopheyl rings of each compound were juxtaposed a remarkable degree of similarity can be seen along their entire vertical axes (FIG. 1B). Complete superimposition of the diiodophenyl rings leads to the structures shown in FIG. 1C and, rotated 90° along their "vertical" axes, FIG. 1D. A striking homology exists between the van der Waals surfaces of each drug use. The lower portion of the superimposed structures containing the inner and outer rings of triiodothyronine displays the greatest degree of similarity. This portion of the T3 has been proposed to interact with the receptor protein. *J. Med. Chem.*, 20:863 (1977). This portion of amiodarone is more flexible than the outer ring of T3. However, the upper portion of the structures, containing benzofuran and its 2-butyl adduct, is most dissimilar, suggesting a structural basis for antagonism. Most strikingly, the butyl group lies spatially in an area completely vacant from T3 occupation. This may account for certain antagonist properties of amiodarone. However, amiodarone has limited utility as a thyroid hormone antagonist because of certain properties. These properties are the drug's slow affinity for the thyroid hormone receptor, probably due to the spatial dissimilarity of its lower portion in space A, numerous amiodarone-induced toxic side effects, and reported amiodarone effects that are not related to thyroid hormone activity, such as for example, amiodarone' sinhibition of in vitro phospholipase $A_1$ production in rat alveolar macrophages, J-774 macrophages and rat liver when used at concentrations 5–10 times greater than that required to inhibit T3 receptor binding by 50%. *Biochem. Biophys. Acta.*, 875:400 (1986). Finally, the drug has a long half-life and accumulates extensively in tissues which could hinder the ability to regulate the actions of the drug.

Nevertheless, the present invention demonstrates that amiodarone interacts directly albeit with low affinity, with the nuclear thyroid hormone receptor, and that it antagonizes the effect of hormone on the production of hormonally induced rat growth hormone RNA. In addition, it indicates that other amiodarone-like (e.g., 4-substituted, HO-O-substituted 2,6-diiodophenol) derivatives have the potential to be of considerable practical value both clinically as cardiotherapeutic drugs and as tools for further investigating the molecular mechanisms of thyroid hormone action, as is disclosed in the present invention.

The N-alkyl compounds of triiodothyronine are described more specifically in the Examples. However, one useful approach is to protect the carboxyl group of triiodothyronine by conversion to an ester using an alcohol (e.g. butyl) and trifluoroacetic anhydride as a catalyst. The ester is then treated with an alkyl halide (e.g. butyl bromide) and recovered. The ester is then converted to the carboxylic acid T3-derivative, using techniques such as treatment with base such as 1-N sodium hydroxide.

UTILITY

This invention is useful for fast, efficient, easy and economical evaluation of pharmacological properties of drugs having certain three dimensional structural atom arrangement. When the spatial arrangement is similar to that of a known pharmacologically active compound and when the pharmacological activity can be confirmed by simple laboratory assay, the probability is high that such compound will have the same-agonistic, or contrary antagonistic activity.

A preferred pharmaceutical use of the compounds selected by this method is in the treatment of thyroid hormone disorders such as hyperthyroidism and hypothyroidism.

The useful pharmacological properties are selected to treat a condition of hyperthyroidism, obesity, angina pectoris, antiadrenergism, cardiac arrythmia, cardiac ischemia or neurologic and psychiatric disorders and conditions in humans.

The following examples are meant to be explanatory and illustrative only and are not to be construed as being limiting in any way.

EXAMPLE 1

N-NORMAL-BUTYL TRIIODOTHYRONINE (a) Commercially available triidothyronine (1 eq.) is combined with normal butyl alcohol (1.1 eq.) in the presence of a trace of an esterification catalyst trifluoroacetic anhydride, in 200 ml of solvent of dimethylformamide. The reaction mixture is held at ambient temperature overnight and then carefully heated to 50° C. for one hour. The butyl carboxylic ester is obtained after a careful aqueous work up using brine. The phenol and amine functional groups increase solubility in water.

(b) The carboxylic ester obtained is then dissolved in about 500 ml of dimethyl formamide. To this solution is added at ambient temperature dropwise butyl bromide (1 eq.) in an equivalent volume of dimethyl formamide. After butyl bromide is added, the reaction mixture is held at ambient temperature overnight (20 hr.) and then heated to 50° C. for 1 hour. The reaction mixture is contacted with water/ice and the organic portion is removed using methylene chloride. The methylene chloride is removed under vacuum. The butyl carboxylate ester-normal-butyl amine, is separated, recovered and purified using column chromatography-hexane/chloroform (50/50) silica gel from any homologs formed.

(b') when a 2.5 or greater excess of butyl bromide is used in step (b), the dibutyl amine derivative is a product and is isolated using column chromatography.

(c) The butyl carboxylate ester normal-butyl amine of step 1(b) above (0.1 eq.) is then dissolved in dimethylformamide and sodium hydroxide (1-N) is added (0.01 eq.) at ambient temperature. After addition, the reaction mixture is held at ambient temperature (20 hr.) and then heated to 40° C. for 1 hr. The carboxylic acid normal butyl amine derivative is obtained by extraction using hexane/chloroform and purified using column chromatography silica gel (hexane/chloroform, 50/50).

EXAMPLE 2

N-ISOBUTYL TRIIODOTHYRONINE

Example 1 is repeated except that in step (a) normal butyl alcohol is replaced with a stoichiometrically equivalent amount of isobutyl alcohol, and in step (b) the normal butyl bromide is replaced with a stoichiometrically equivalent amount of isobutyl bromide. The N-isobutyl triiodothyronine is obtained.

EXAMPLE 2A

Example 1 is repeated except that in step (a) tertbutyl alcohol is replaced with a stoichiometrically equivalent amount of isobutyl alcohol, and in step (b) the tertiary butyl bromide is replaced with a stoichiometrically equivalent amount of isobutyl bromide. The N-tertbutyl triiodothyronine is obtained.

EXAMPLE 3

Method for Selecting Compounds Expected to Have Pharmacological Activity

This example illustrates the method of evaluation and selection of compound and predicting their pharmacological activity based on their three dimensional spatial atom arrangement.

A. Three Dimensional Space Plane

Three dimensional x, y, z coordinate axes plane was designed, as shown in FIG. 3, according to the procedure described in *Advanced Physical Chemistry*, Ed. S. M. Blinder, MacMillan Co., London, U.K. (1969).

B. Choice and Preparation of Standard and Experimental Compounds

Standard compound was chosen to be triiodothyronine (T3) as shown in FIG. 2B.

The experimental compound was chosen to be benzofurane compound amiodarone as shown in FIG. 2A. Amiodarone was chosen to prove the validity of the current invention because it is seemingly and visibly, not structurally similar to the standard compound T3 as seen by comparison of FIGS. 2A and 2B. By its pharmacological activity, however, there is some evidence pointing toward its possible T3 antagonist function.

C. Computer Modeling of Standard and Experimental Compounds

Commercially available computer a VAX®, obtained from Digital Equipment, Maynard, Mass., using VMS® or UNIX® computer software operating systems and MM2® computer software program obtained through the Quantum Chemistry Program Exchange, University of Indiana, Bloomington, Ind. was used to extract the coordinates of T3. These coordinates were confirmed by the Cambridge Crystallographic Structural Data Base, Medical Foundation of Buffalo, N.Y.

Drug design computer software computer program SYBYL®, obtained from Tripolis Associates, St. Louis, Mo., BIOGRAPH® computer software program, obtained from Biodesign, Pasadena, Calif., and MIDAS® computer software program, obtained from the (Computer Graphics Laboratory of the University of California, San Francisco, Calif.), were also loaded on the VAX® computer.

The coordinates of both T3 and amiodarone obtained either from crystallographic studies or by standard data sets were input into the VAX computer and energy refinements were performed using the MM2® computer software program. Computer modeling was performed at the Computer Graphics Laboratory of the University of California, San Francisco. The compounds were modelled in extended conformation using standard geometries. Coordinates were displayed and manipulated in real time with the MIDAS® computer software program on a Silicon Graphics IRIS 80 GT® computer system, a trademark of and available from Silicon Graphics, Inc. of Mountain View, Calif.

First the three dimensional model of T3, using the available coordinates, was displayed on the screen, on which the model of amiodarone, using the available coordinates was superimposed. The structure model of amiodarone was then manipulated by manipulating its spatial structural atoms together with manipulating the spatial structural atoms of T3.

In the computer models, both T3 and amiodarone were displayed with their respective computer generated van der Waals surfaces displayed around individual atoms. Where the diiodphenyl rings of both molecules were juxtaposed, a remarkable degree of similarity has been seen along their entire vertical axes, as shown in FIG. 1B. Complete superimposition of the diiodophenyl rings led to structures shown in FIG. 1c. Only very small torsion angle adjustments were required in order to superimpose the molecular structures. When both models were rotated 360° through space along their vertical axes, a striking homology was found between the van der Waals surfaces of both compounds T3 and amiodarone as shown in FIG. 1D (at 90° rotation). The lower portion, i.e., on -y axis of the superimposed structures containing the inner and outer rings of T3 displays the greatest degree of similarity. This portion has been proposed (*J. Med. Chem.*, 20:863 (1977)), to be responsible for T3 interaction with the receptor. On the other hand, the structural dissimilarity exist between the upper portion of the structures, containing benzofuran and its 2-butyl adduct. This dissimilarity points toward and provides basis for antagonistic properties of amiodarone.

These observations were confirmed by biological and pharmacological tests shown in Example 4.

EXAMPLE 4

Pharmacological Testing of Amiodarone for Its Antagonistic Activity

This example describes a series of biological and pharmacological tests performed to confirm the antagonistic activity of amiodarone which has been predicted by the computerized three dimensional structural examination of amiodarone spatial arrangement as described in Example 3.

Cell Culture utilized GC cells obtained from the cellular culture facility at UCSF. GC cells were plated at $2-4\times10^6$ cells/100 mm tissue culture disk obtained from Falcone, and were maintained at 37° C., in the mixture of $O_2/CO_2$ 95/5%, in DMEM 21 medium containing 10% of fetal calf serum, obtained from J. R. Scientific, Woodland, Calif., to which 100/ml of penicillin and streptomycin, and 2 mM of glutamine were added.

Thyroid hormones T3 and thyroxine T4 were removed from fetal calf serum with AG 1-X8 ion exchange resin from Biorad, Hercules, Calif. by the method described in *Endocrinology*, 105:80 (1979). Before treatment, T4 and T3 concentrations were determined to be $1.9\times10^{-7}$ and $1.9\times10^{-9}$M, respectively. Following the treatment, in 100% thyroid hormone depleted (stripped) serum, T4 and T3 were $1.7\times10^{-8}$ and non-detectable (less than 300 pM), respectively. Actual concentrations in 2% media were therefore 1/50 of those values.

Solubilized T3 nuclear receptors were prepared from rat liver according to procedure described in *J. Biol. Chem.*, 263: 9409–9417. Solubilized nuclear receptors from the whole rat brain were prepared by the method described in *Endocrinology*, 103:943 (1978). Solubilized receptors from GC cells were prepared as follows. Confluent 150 cm² culture plates were rinsed for 5 minutes with PBS at 37° C. and scraped with a rubber policeman in 5 ml PBS at 4° C. the 1000 xg cell pellet was suspended in 10 ml of Solution 1 consisting of 20 mM $KPO_4$, 4 mM EGTA, 4 mM $MgCl_2$, 0.25M sucrose, 0.5% NP-40, 0.5 mM PMSF, and 0.1% of MTG, having pH 7.6 and put on ice for 3 minutes. Suspension was centrifuged and cell lysate was washed with Solution A minus NP-40, centrifuged again and the pellet was resuspended in 10 ml of Solution B consisting of 20 mM $KPO_4$, 10 mM EDTA, 2 mM $MgCl_2$ having pH 7.2. The nuclei obtained above were gently mixed and allowed to sit at 300 xg for 10 minutes and there resulting chromatin pellet was washed twice in 10 ml of Solution C consisting of 10 mM $KPO_4$, 1 mM $MgCl_2$, 0.1% MTG having pH 7.2. The washed pellet was then solubilized in 2 ml of Solution D consisting of 10 mM Tris, 1 mM $MgCl_2$, 0.5 mM EDTA, 400 mM KCl, 10% glycerol, 0.1% MTG, having pH 7.6. The chromatin was then sonicated in Solution D 30×1 second pulses. After 30 minutes incubation on ice, polyethyleneimine (PEI) was added to a final concentration of 0.01% and the solution was stirred gently for 5 minutes. Following centrifugation at 15,000×g for 15 minutes, the supernatant was adjusted with 3% PEG, 0.02% PEI and 20 mM $KPO_4$. After 20 minutes on ice, this suspension was centrifuged again at 15,000×g for 30 minutes and aliquots were removed, frozen in liquid $N_2$ and stored at −70° C. Treatment with PEI was introduced to remove any contaminating DNA. Yield of the procedure was 7.5 pmol for 900×$10^6$ cells having specific activity of 3.1 pmol/mg of protein and containing 5000 receptor sites per cell.

For in vitro binding assay, thyroid hormone receptor preparations, as described above, were incubated with varying concentrations on nonradioactive T3 or amiodarone for 18 hours at 4° C. in a buffer consisting of 20 mM $KPO_4$, 0.5 mM EDTA, 1 mM $MgCl_2$, 400 mM KCl, 8% glycerol and 0.1% MTG. Bound and free labeled $^{124}$54 I-T3 were separated with G-25 sephadex. Receptor concentrations were determined to be 150–300 pM. L-T3 was obtained from Aldrich Chemicals. A 1 mM stock solution was prepared in MeOH containing 1% $NH_4OH$. This solution was diluted in 0.1 mM NaOH and added directly to binding and culture assays. Stock solutions of amiodarone-HCl, obtained Sanofi Chemicals, France, were prepared fresh at 14 mM in EtOH:10 mM HCl (1:1). Dilutions were prepared in 1 mM HCL. L-$^{125}$ I-T3 NEX-110X, 2200 Ci/mmol was obtained from New England Nuclear.

Binding of $^{125}$I-T3 to nuclear receptors of intact GC cells was achieved by plating two million cells per well of G-well tissue culture plates of 9.3 $cm^2$/well in 3 ml of media. After 18 hours, cells were rinsed with 1 ml of PBS for 10 minutes at 37° C. and incubated for four hours in DMEM containing 10% serum substitute solution and 2% stripped calf serum. For competition assays, cells were incubated in 1 ml of stripped media containing 300 pM of $^{125}$I-T3 and various doses of amiodarone. Incubations were carried out at 37° C. on a Tilt table. After 3 hours during which time equilibrium was established, cell nuclei were prepared by lysis in situ and specific nuclear binding determined according to established methods for pituitary tumor cells according to procedure described in *Proc. Natl. Acad. Sci.*, 70:3488 (1973). Binding in each nuclear pellet was normalized to DNA content, which was determined according to *Biochem. J.*, 62:315 (1956). Under these conditions maximum binding capacity was about 85 fmol/100 ug DNA. Relative to L-T3, no effect of amiodarone on cell surface transport of $^{125}$I-T3 was observed.

Analysis of receptor binding parameters was done and binding data were analyzed with SCATFIT®, a computer software program available from the University of California, San Francisco and ALLFIT®, a computer software program available from the University of California, San Francisco described in *Am J. Physiol.*, 235 E97-E102 (1978), and *Molec. Pharm.*, 21:5–16 (1982). These programs perform non-linear, least squares model fitting utilizing untransformed data by sequential interaction of binding parameters and generate $K_d$, Bmax, pseudo-Hill slope constant (b) and $EC_{50}$ parameters. The ability of amiodarone to compete with T3 for binding to the thyroid hormone receptor was assessed by comparison of $K_d$ and $EC_{50}$ values generated by the Scatfit and Allfit programs, respectively.

Preparation and Quantitation of Cytoplasmic RNA was done by plating and attachment for 12–18 hours of GC cells, followed by deinducing 4 days in 20 ml of DMEM containing 10% serum substitute solution obtained from Cell Culture Facility, UCSF, and 2% of stripped serum, prepared above. Media were replaced after the second day of deinduction. After 4 days of deinduction, cells were cultured for additional two days in stripped media containing either (1) 300 pM T3 plus one of the following dose of amiodarone: 0, 10 mM, 100 mM, 1 uM or 10 uM; or (2) no additional treatment (NT). Total cytoplasmic mRNA was prepared according to *Methods Enzymol.*, 65:718 (1980).

The amount of rGH message present in aliquots of GC cell cytoplasm was determined by Northern hybridization using glyoxylated RNA (*Ibid.*, p. 380). Equal amounts of cytoplasmic RNA were examined per lane (15 or 20 ug). HeLa cell RNA was also tested as a control for specificity and background binding. The rGH message was detected by hybridization with the 0.8 kbpRGH-1 rat growth hormone cDNA according to *Nature*, 270:486 (1977). Some blots were also probed with a 1.6 kb Kho I fragment of the pHF1 human gamma-actin gene according to *Mol. Cel. Biol.*, 3: 787 (1983). Both probes were labelled by Nick translation with $^{32}$P-dCTP, obtained from Amersham to 3–5×$10^8$ cpm/ug according to *J. Mol. Biol.*, 113:237 (1977). Hybridizations were carried out for 18–48 hours at 42° C. Blots were autoradiographed with Kodak XAR-2 film using Cronex Lightning plus intensifying screens.

The results of the studies are summarized in Table 1 and in FIGS. 5–7.

Using crude preparations of KCl-solubilized rat liver nuclei, T3 was shown to bind with high affinity to a single class of receptor cites, ($K_d$=359 pM). This value was used was an initial estimate of receptor affinity for other studies.

TABLE 1C

| | Binding Affinities | | | |
|---|---|---|---|---|
| | Triiodothyronine | | Amiodarone | |
| Receptor Source | $K_d$ | *b | $K_d$ | b |
| Liver | 3.7 ± 0.1 × $10^{-10}$M | 1.0 ± 0.1 | 7.2 ± 2.1 × $10^{-6}$M | 0.9 ± 0.1 |

TABLE 1C-continued

| | Binding Affinities | | |
|---|---|---|---|
| Brain | | $13.7 \pm 1.6 \times 10^{-6}$M | $1.0 \pm 0.1$ |
| GC cell | $5.6 \pm 1.7 \times 10^{-10}$M | $1.6 \pm 0.2 \times 10^{-6}$M | $0.7 \pm 0.1$ |
| | $EC_{50}$ | $EC_{50}$ | |
| GC Nuclear Binding (intact cells) | $8.7 \pm 0.2 \times 10^{-10}$M   $1.0 \pm 0.1$ | $3.3 \pm 0.2 \times 10^{-6}$M | $0.9 \pm 0.4$ |

*b is a slope factor determined with Allfit program.

Values for b did not differ significantly from 1.0. Effective Concentration ($EC_{50}$) is the apparent concentration of agonist T3 or antagonist amiodarone needed to decrease binding of $^{125}$-I T3 (300 pM) to 50% maximum values.

Table 1C shows binding affinities ($K_d$) of T3 and amiodarone to solubilized nuclear receptors of rat liver, brain, pituitary tumor cells or in intact cultured cells. $K_d$ values were determined by competition binding studies and analyzed by weighted, non-linear least squares regression with the aid of the Scatfit computer program. Affinities derived from liver receptor preparations represent the weighted means from six experiments. Other values represent the mean of at least two experiments.

While amiodarone competed with $^{125}$I-T3 for binding to solubilized receptors from pituitary tumor cells of the GC cell line with $K_d$ of 1.6 µM, the affinity for receptors from rat brain of $K_d$ 13.7 37 µM was smaller, suggesting that amiodarone interacted differently with the brain receptors than with GC cell receptors. When both T3 and amiodarone were incubated with intact cells, both T3 and amiodarone competed with labeled T3 for binding to the thyroid hormone receptors, as shown by their $EC_{50}$ values in Table 1.

In a variety of solubilized receptor preparations, amiodarone competed with T3 for binding to a single class of sites in a dose-dependent fashion at concentrations from $10^{-7}$ to $10^{-4}$M as shown in FIG. 5. For rat liver receptor, the 50% inhibition ($EC_{50}$) occurred at 3 µM amiodarone and 80% inhibition was at 50 µM.

FIG. 5 shows a competition by unlabelled L-T3 and amiodarone for binding of L- $^{125}$I-T3 to rat nuclear thyroid hormone receptors solubilized from various tissues. Pictured are competition curves for T3 in liver receptors (open circles); and for amiodarone in liver (closed circles), whole brain (closed boxes), and GC cell receptors (closed triangles). The affinity ($K_d$) for T3 in liver nuclear receptors was $3.7 \times 10^{-10}$M. In the individual experiments shown, affinities for amiodarone were 1.4 µM, 13.7 µM and 2.9 37 µM in solubilized receptors from rat liver, brain and pituitary tumor (GC) cells, respectively. [R]-160–280 pM. $^{125}$I-I3 is 100–200 pM.

The competitive nature of amiodarone binding was investigated by using 10 µM amiodarone on the binding of increasing doses of $^{125}$I-T3 to soluble nuclear receptors, computer modeling of these curves revealed an amiodarone Ki of 9.3 µM for a single class of sites, which was not statistically different from 7.2 µM obtained with a fixed amount of $^{125}$I-T3 and with varying concentration of amiodarone. Increasing concentrations of T3 reversed amiodarone's effect on T3 binding which is characteristic of a competitive binding inhibitor. The data shown in FIG. 6 are redrawn as a Lineweaver-Burk plot.

Figure 6B:
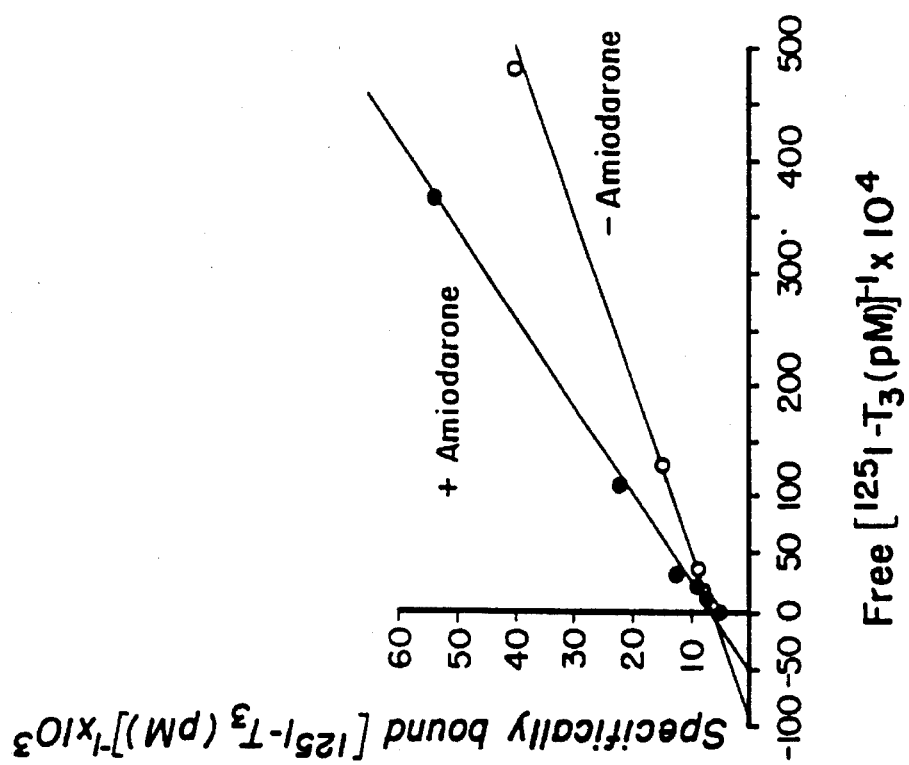
Figure 6A:
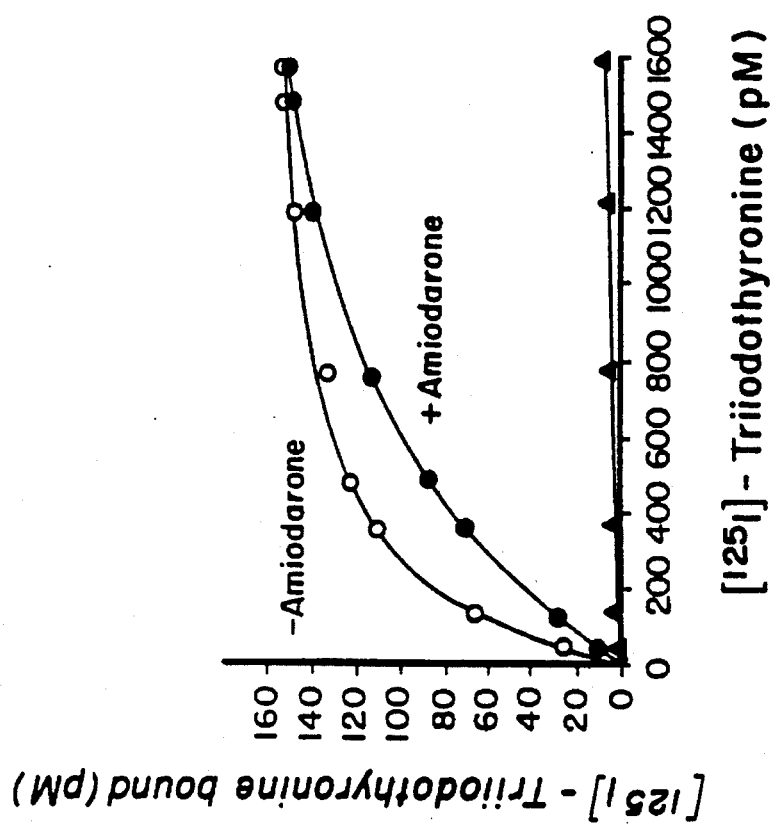

FIG. 6 shows effects of amiodarone on saturation binding T3 to soluble nuclear receptors. FIG. 6a shows saturation binding isotherms where 10 pM of soluble rat liver nuclear receptor (3 pmol/mg) was incubated with increasing amounts of $^{125}$I-T3 in the absence ($K_d$) and presence ($K_d'$) of inhibitor, and these values were used to determine a $K_i$ for amiodarone. In these experiments more pure preparations of rat liver receptor were utilized than before. The following values were obtained from computer modeling: $K_d$=108 pM, $K_d'$=224 pM, and $K_i$ 9.3 µM. The lower line (closed triangles) indicates non-specific binding (average of both curves), which represented 2–4% of total binding. Binding of $^{125}$I-T3 in the presence of 1 µM unlabeled T3 yields values for non-specific binding (NSB). Separation of bound from free T3 was achieved with SEPHADEX®, a trademark for a dry insoluble powder of microscopic beads of synthetic organic compounds derived from the polysaccharide dextran held by Pharmacoepia, Inc. FIG. 6b shows Lineweaver-Burk transformation of the data. The abscissa (x) and ordinate (y) represent the inverse of free pM $^{125}$I-T3 and pM $^{125}$I-T3 specifically bound, respectively. The slopes (b) of the regressions in the absence and presence of amiodarone were 0.07±0.00 and 0.13±0.00, respectively (b±95% C.I.). The calculated $K_i$ from these slopes using the less accurate graphical methods was 11.6 µM. The y-intercepts (a) were 6.6±0.2 and 6.8±0.7 (a±SEE), respectively, indicating that maximum binding did not differ in the absence or presence of amiodarone. $r^2$=0.99 for each regression line.

The GC culture cells were further utilized to assess the effect of the amiodarone on T3 action. These cells respond to T3 by increasing their synthesis of rat growth hormone (rGH) due to increases in rGH mRNA resulting from transcriptional activation of the growth hormone gene. As shown in FIG. 7a, amiodarone blocked the induction of rGH mRNA by 300 pM T3 as analyzed by RNA blot using Northern analysis. FIG. 7b displays an amiodarone mRNA competition curve and as can be seen, the $EC_{50}$ for blockade of rGH mRNA by amiodarone was 3.1 µM, very similar to the $EC_{50}$ for binding to the thyroid hormone receptor in the presence of 300 pM T3, identical experimental conditions.

FIG. 7 shows effects of amiodarone on accumulation of rGH mRNA and on binding by T3 to nuclear fractions of cultured GC cells.

FIG. 7A is a autoradiogram of a representative Northern blot of rGH nRNA from GC cell cytoplasm. GC cells were plated at 2–4×10⁶ cells/100 mm tissue culture dish (Falcon) and were maintained at after four days of deinduction, cells were cultured for an additional 2 days in the presence of stripped media containing 300 pM T3 plus varying doses of amiodarone as described above.

FIG. 7B, open circles shows composite mRNA response curve constructed from 4 amiodarone experiments with cultured GC cells. After treatment with T3 and graded doses of amiodarone, cytoplasmic RNA was prepared and analyzed by Northern hybridization as described in above. After hybridization, blots were autoradiographed and analyzed using Zenith scanning densitometer. Arbitrary density units were used to construct competition curves and to derive $EC_{50}$ values and slope factors for amiodarone's effect on rGH mRNA accumulation. The "100%" point on the curve represents data from cells treated with 300 pm T3 without amiodarone. The circled point represents data from non-treated cells.

Closed circles show amiodarone inhibition of binding of $^{125}I$-T3 to nuclei of intact GC cells.

These results of various pharmacological and biological tests show that amiodarone acts as a competitive antagonist to thyroid hormone action. These results also show that amiodarone binds to thyroid hormone receptors from a variety of tissues and inhibits T3 induced increases in growth hormone mRNA levels in GC cells in a similar dose-dependent manner, and are in agreement with the discovery that spatial atom arrangements, determined in Example 3, of lower portion of the amiodarone are similar to that of T3, but spatial atom arrangement of amiodarone's upper portion is dissimilar to T3.

EXAMPLE 5

Evaluation of Compounds' Pharmacological Activity

This example illustrates the utility of the current invention for evaluation and/or prediction of compounds pharmacological activity.

Representative compounds from groups of $R^1$ and $R^2$ substituents were chosen to be evaluated first by the procedure described in Example 3. Their coordinates were determined and input into VAX computer and the three dimensional models were prepared. Then the structural three dimensional models were superimposed on the T3 model structure and both models were manipulated to prove or disprove the spatial fit. When the fit was there, a binding study to the T3 receptor was performed.

Only when both the spatial fit and receptor binding was found, the compound was recommended for further pharmacological testing to determine its possible pharmaceutical utility.

For the compounds listed below, receptor binding studies were performed in a manner entirely analogous to the examples previously given, with the exception of the source of the receptor. In FIGS. 8–13, human thyroid hormone receptor was produced by in-vitro translation of RNA coding for the receptor protein. The RNA was synthesized enzymatically using a human thyroid receptor DNA clone as a template. Such a system has been described previously as in *Nature*, 324: 635 and 641 (1986).

FIGS. 8–13 illustrate the thyroid receptor binding results.

FIG. 8 serves as a standard with $^{125}I$-T3 and amiodarone, which was already shown to have spatial fit and receptor binding. For structures, see FIGS. 2A and B.

FIG. 9 shows the following compound:

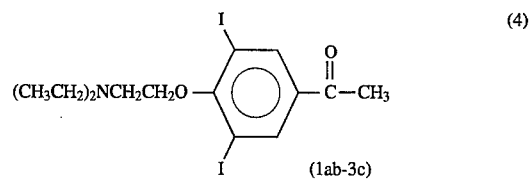

This compound structurally fitted when its model was superimposed over the structure (1) model. When however submitted to the receptor binding assay, there was zero binding. For FIGS. 8–13, □ show $^{125}I$-T3, ♦ show experimental compound. The compound was not recommended for further pharmacological testing.

FIG. 10 shows the following compound:

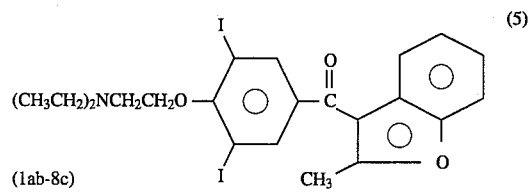

This compound substitutes a methyl for the butyl group of amiodarone. This compound has spatial fit when superimposed over the model space structure (1) and also shows good binding to T3 receptor.

It was strongly recommended for further pharmacological testing.

FIG. 11 shows the following compound:

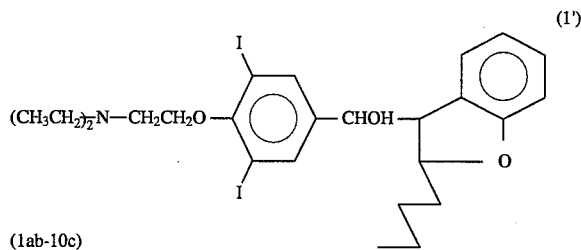

This compounds binds weakly to the T3 receptor, but since it binds, it was recommended for further testing with the expectation that either agonist or antagonist function will be found.

FIG. 12 shows the following compound:

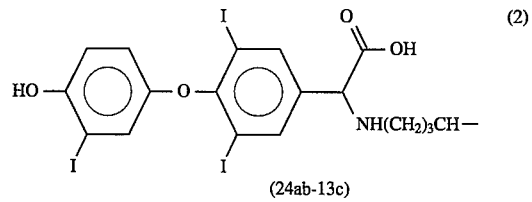

This compound fits within the spatial arrangement of the space structure (1) model and binds to the T3 receptor.

It was recommended for further pharmacological testing.

FIG. 13 shows the following compound:

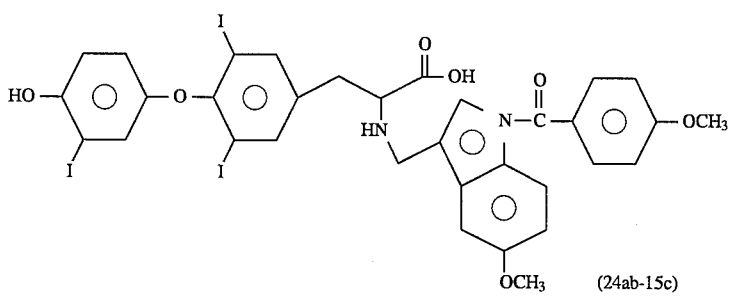

(3)

(24ab-15c)

This compound fits within the spatial arrangement of the structure (1) model and binds to the T3 receptors.

It was recommended for further testing.

Similarly to the compounds 1–5, all other compounds are tested first for their spatial fit to the structure (1) and then for their binding property to the T3 receptor.

EXAMPLE 6

General utilization of the spatial Fits and Receptor Binding for Pharmaceutical Industry This example illustrates the general utilization of the method of this invention for evaluation, prediction and design of the pharmacological activity of known or novel compounds of which structure can be, via its coordinates, entered into the computerized system of this invention and compared to any standard compound of which the spatial model can be modelled into three dimensional spatial model and which is active as either agonist or antagonist of receptors which are isolated and for which the binding assay is available.

While only a few embodiments of the invention have been shown and described herein, it will become apparent to those skilled in the art that various other modifications and changes can be made a) in the present method to select compounds useful as pharmacologically active agents in a mammal, b) to the compounds themselves, c) their method of preparation, and d) their pharmaceutical use without departing from the spirit and scope of the present invention. All such modifications and changes are intended to be within the scope of the invention and appended claims.

What is claimed is:

1. A method for selecting and evaluating pharmacological activity of an experimental chemical compound, which method comprises steps:

(a) selecting a standard chemical compound having known chemical structure and known pharmacological activity and preparing a three dimensional spatial atom arrangement model of the standard chemical compound wherein the standard chemical compound is spatially defined as a volume by conventional cartesian three dimensional x, y, z coordinate space axes planes;

(b) choosing an experimental chemical compound structure to be evaluated;

(c) preparing a computer created three dimensional spatial atom arrangement model of the experimental compound of step (b) wherein the experimental compound is also defined by a conventional cartesian three dimensional x, y, z coordinate space axes planes;

(d) displaying and superimposing the model of the experimental chemical compound of step (c) over the model of the standard chemical compound of step (a) on the computer screen;

(e) determining three-dimensional spatial similarities or dissimilarities of the standard chemical compound structure of step (a) with the experimental chemical compound structure to be evaluated of step (c) by manipulating both models on the computer screen;

(f) determining that the spatial atom arrangement of the experimental chemical compound fits maximizing the overlap with the cartesian three dimensional x, y, z coordinate volume defined by the standard compound of step (a) producing a positive or negative matching result and when the spatial matching result is positive;

(g) performing a known pharmacological test, in which the standard compound of step (b) to determine whether or not the experimental compound is active in said known pharmacological test producing a positive or negative result; and (h) selecting for further pharmacological evaluation only the experimental chemical compound wherein step (f) and step (g) have positive results, wherein the models of a standard chemical compound structure and the chosen experimental compound chemical structure to be evaluated are prepared by:

(A) obtaining coordinates of the models of the standard and experimental compounds from the computer which uses at least one computer operating system and at least one computer software program;

(B) entering the coordinates of both the standard compound and the compound to be evaluated into the computer;

(C) performing energy refinement using the computer software program;

(D) modeling both compounds in extended conformation using standard geometries;

(E) displaying coordinates x, y, z on the screen and manipulating these coordinates in real time with the computer software program on a graphic system;

(F) superimposing the volume model of the experimental compound to be evaluated over the volume model of the standard compound;

(G) manipulating both models on the computer screen by displaying their structural models with their respective computer generated Van der Waals surfaces around individual atoms;

(H) rotating both models 360° through space along the vertical axis;

(I) observing and recording similarities along the x, y, z axes;

(J) evaluating the experimental compound as having structural similarity or dissimilarity with the standard compound;

(K) determining that the spatial atom arrangement of the experimental chemical compound fits maximizing the overlap with the cartesian three dimensional x, y, z coordinate volume defined by the standard compound of step (A) producing a positive or negative matching result and when the spatial matching result is positive;

(i) performing a known pharmacological test, in which the standard compound of step (A) is active, on the experimental compound of step (B) to determine whether or not the experimental compound is active in said known pharmacological test producing a positive or negative result; and (j) selecting for further pharmacological evaluation only the experimental chemical compound wherein step (K) and step (i) have positive results, wherein the three dimensional model of experimental compound is superimposed over the three dimensional model of the standard compound and both structures are oriented along their vertical y axis until their spatial similarities or dissimilarities are shown.

2. The method of claim 1 wherein the similarities are due to the compound's atoms van der Waals characteristics.

3. The method of claim 2 wherein the orienting of the compound structure, preparing three dimensional models, superimposing models and orienting models by rotation into conformational spaces is done by computer.

4. The method of claim 3 wherein the pharmacological activity of the standard compound is determined by receptor binding assay.

5. The method of claim 1 wherein the pharmacological activity of the standard compound is determined by receptor binding assay.

6. A method for selecting and evaluating pharmacological activity of an experimental chemical compound, which method comprises steps:

(a) selecting a standard chemical compound having known chemical structure and known pharmacological activity and preparing a three dimensional spatial atom arrangement model of the standard chemical compound wherein the standard chemical compound is spatially defined as a volume by conventional cartesian three dimensional x, y, z coordinate space axes planes;

(b) choosing an experimental chemical compound structure to be evaluated;

(c) preparing a computer created three dimensional spatial atom arrangement model of the experimental compound of step (b) wherein the experimental compound is also defined by a conventional cartesian three dimensional x, y, z coordinate space axes planes;

(d) displaying and superimposing the model of the experimental chemical compound of step (c) over the model of the standard chemical compound of step (a) on the computer screen;

(e) determining three-dimensional spatial similarities or dissimilarities of the standard chemical compound structure of step (a) with the experimental chemical compound structure to be evaluated of step (c) by manipulating both models on the computer screen;

(f) determining that the spatial atom arrangement of the experimental chemical compound has maximum overlap with the cartesian three dimensional x, y, z coordinate volume defined by the standard compound of step (a) producing a positive or negative matching result and when the spatial matching result is positive;

(g) performing a known pharmacological test, in which the standard compound of step (b) to determine whether or not the experimental compound is active in said known pharmacological test producing a positive or negative result; and (h) selecting for further pharmacological evaluation only the experimental chemical compound wherein step (f) and step (g) have positive results, wherein the models of a standard chemical compound structure and the chosen experimental compound chemical structure to be evaluated are prepared by:

(A) obtaining coordinates of the models of the standard and experimental compounds from a crystallographic database or from the construction of three dimensional models by the use of three dimensional molecular modelling software at least one computer operating system and at least one computer software program;

(B) entering the coordinates of both the standard compound and the compound to be evaluated into the computer;

(C) performing energy refinement of the molecular model using a molecular mechanical or quantum mechanical optimization and energy minimization computer software program;

(D) modeling both compounds in extended conformation using optimized geometries as determined in steps (A) and (C);

(E) displaying coordinates x, y, z on the screen and manipulating these coordinates in real time with the computer program on a graphic system;

(F) superimposing the volume model of the experimental compound to be evaluated over the volume model of the standard compound;

(G) manipulating both models on the computer screen by displaying their structural models with their respective computer generated Van der Waals surfaces around individual atoms;

(H) rotating and translating both models through space until overlap of the standard structure and experimental structure is maximized;

(I) observing and recording similarities along the x, y, z axes;

(J) evaluating the experimental compound as having structural similarity or dissimilarity with the standard compound;

(K) determining that the spatial atom arrangement of the experimental chemical compound fits maximizing the overlap with the cartesian three dimensional x, y, z coordinate volume defined by the standard compound of step (A) producing a positive or negative matching result and when the spatial matching result is positive;

(L) performing a known pharmacological test, in which the standard compound of step (A) is active, on the experimental compound of step (B) to determine whether or not the experimental compound is active in said known pharmacological test producing a positive or negative result; and (M) selecting for further pharmacological evaluation only the experimental chemical compound wherein step (K) and step (L) have positive results, wherein the three dimensional model of experimental compound is superimposed over the three dimensional model of the standard compound and both structures are rotated and translated along their vertical y axis until their overlap is optimized and their spatial similarities or dissimilarities are shown.

7. The method of claim 6 wherein the similarities are due to the compound's atoms van der Waals characteristics.

8. The method of claim 7 wherein the orienting of the compound structure, preparing three dimensional models, superimposing models and orienting models by rotation into conformational spaces is done by computer.

9. The method of claim 8 wherein the pharmacological activity of the standard compound is determined by receptor binding assay, binding assay or enzyme assay.

10. The method of claim 6 wherein the pharmacological activity of the standard compound is determined by receptor binding assay, binding assay or enzyme assay.

* * * * *